(12) United States Patent
Swiston et al.

(10) Patent No.: US 8,323,637 B2
(45) Date of Patent: Dec. 4, 2012

(54) SYNTHETICALLY FUNCTIONALIZED LIVING CELLS

(75) Inventors: Albert J. Swiston, Baltimore, MD (US); Michael F. Rubner, Westford, MA (US); Robert E. Cohen, Jamaica Plain, MA (US); Darrell J. Irvine, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 717 days.

(21) Appl. No.: 12/421,162

(22) Filed: Apr. 9, 2009

(65) Prior Publication Data

US 2009/0258057 A1 Oct. 15, 2009

Related U.S. Application Data

(60) Provisional application No. 61/043,592, filed on Apr. 9, 2008.

(51) Int. Cl.
*A01N 63/00* (2006.01)
*C12N 11/00* (2006.01)
*C12Q 1/00* (2006.01)

(52) U.S. Cl. ............................ 424/93.1; 435/4; 435/174

(58) Field of Classification Search ........................ None
See application file for complete search history.

(56) References Cited

U.S. PATENT DOCUMENTS

| 7,067,306 | B2 | 6/2006 | Singhvi et al. | |
|---|---|---|---|---|
| 2003/0157260 | A1* | 8/2003 | Rubner et al. | 427/402 |
| 2003/0215626 | A1 | 11/2003 | Hiller et al. | |
| 2004/0026615 | A1* | 2/2004 | Ellson et al. | 250/288 |
| 2006/0029634 | A1 | 2/2006 | Berg et al. | |

OTHER PUBLICATIONS

Bhat et al., *Advanced Materials*, 17(23), 2802-2807 (2005).
Lee et al., *Langmuir*, 20(10), 4155-4161 (2004).
Chao Yang et al., *The Annuls of Thoracic Surgery*, 81(1), 57-64 (2006).
Vipra Dhir et al., *Biotechnology Progress*, 25(2), 594-603 (2009).
U.S. Appl. No. 10/393,360, filed Mar. 21, 2003, Hiller et al.
Berg et al., *Biomacromolecules*, 7 (1), 357 (2006).
Berg et al., *Langmuir* 19, 2231 (2003).
Berg et al., *Langmuir*, 20 (4), 1362 (2004).
Bhatia et al., *Current Opinion in Colloid & Interface Science* 10 (1-2), 45 (2005).
Boulmedais et al., *Langmuir* 19, 9873 (2003).
Chang et al., *Science* 146 (3643), 524 (1964).
Cho & Caruso, *Macromolecules* 36, 2845 (2003).
Choi & Rubner et al., *Macromolecules*, 38 (1), 116 (2005).
Decher et al., *Science* 277, 1232 (1997).
Diaspro et al., *Langmuir* 18 (13), 5047 (2002).
Fery et al., *Langmuir* 17, 3779 (2001).
Garza et al., *Langmuir* 20, 7298 (2004).
Georgieva et al., *Langmuir* 20 (5), 1895 (2004).
Germain et al., *Biosensors and Bioelectronics* 21(8), 1566 (2006).
Hillberg & Tabrizian et al., *Biomacromolecules*, 7 (10), 2742 (2006).
Hua et al., *Langmuir* 18, 6712 (2002).
Kharlampieva & Sukhishili et al., *Polymer Reviews*, 46 (4), 377 (2006).
Kim et al., *Advanced Functional Materials*, 16 (10), 1313 (2006).
Kim et al., *Biomacromolecules*, 5 (3), 822 (2004).
Krol et al., *Langmuir* 21 (2), 705 (2005).
Lee et al., *Nano Letters* 6, 2305 (2006).
Li et al., *Langmuir*, 22 (24), 9820 (2006).
Li et al., *Macromolecules* 38, 7876 (2005).
Lvov et al., *Chemistry Letters*, 23 (12), 2323 (1994).
Lvov et al., *Thin Solid Films*, 285, 797 (1996).
Lynn et al., *Advanced Materials*, 19 (23), 4118 (2007).
Mendelsohn et al., *Biomacromolecules*, 4 (1), 96 (2003).
Mendelsohn et al., *Langmuir* 16, 5017 (2000).
Moya et al., *Colloids and Surfaces A: Physiochemical and Engineering Aspects* 183-185, 27 (2001).
Ono & Decher, *Nano Letters* 6, 592 (2006).
Orive et al., *Nat Med* 9 1 (1), 104 (2003).
Orynbayeva et al., *Angewandle Chemie International Edition* 44 (7), 1092 (2005).
Park et al., *Advanced Materials* 16, 520 (2004).
Quinn & Caruso et al., *Langmuir*, 20 (1), 20 (2004).
Richert et al., *Langmuir* 20, 448 (2004).
Serizawa et al., *Macromolecules*, 37 (17), 6531 (2004).
Shaikhmohammed et al., *Biomacromolecules* 5, 1745 (2004).
Shaikhmohammed et al., *Langmuir* 22, 2738 (2006).
Shiratori & Rubner et al., *Macromolecules* 33 (11), 4213 (2000).
Sukhishvili & Granick, *Macromolecules* 35, 301 (2002).
Tikhonov et al., *J. Biochem. Biophys. Met.*, 60 (1), 29 (2004).
Uludag et al., *Advanced Drug Delivery Reviews* 42 (1-2), 29 (2000).
Underhill et al., *J. Cell Sci.*, 103 (2), 293 (1992).
Wu et al., *Advanced Materials*, 18 (20), 2699 (2006).
Xia & Whitesides, *J. Am. Chem. Soc.*, 117, 3274 (1995).
Xia et al., *J. Am. Chem. Soc.*, 117, 9576 (1995).
Zheng et al., *Advanced Materials*, 14 (8), 572 (2002).

* cited by examiner

*Primary Examiner* — Debbie K Ware
(74) *Attorney, Agent, or Firm* — Steptoe & Johnson LLP

(57) ABSTRACT

Uniform, functional polymer patches can be attached to a fraction of the surface area of living individual cells. These surface-modified cells remain viable after attachment of the functional patch. The patch does not completely occlude the cellular surface from the surrounding environment. Functional payloads carried by the patch may include, for example, drugs or other small molecules, peptides, proteins, thermally responsive polymers, and nanoparticles, or any other material that can be incorporated in a polymer patch of subcellular dimensions. The patch can include one or more polyelectrolyte multilayers (PEMs).

27 Claims, 18 Drawing Sheets

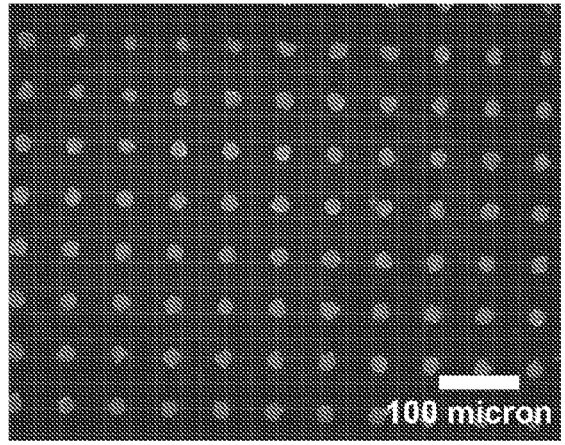
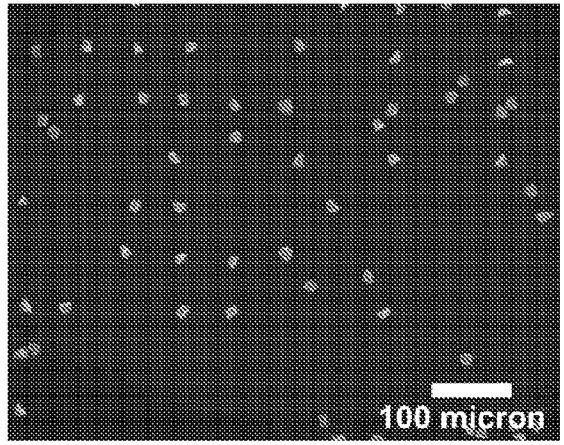
FIG. 8A  FIG. 8B
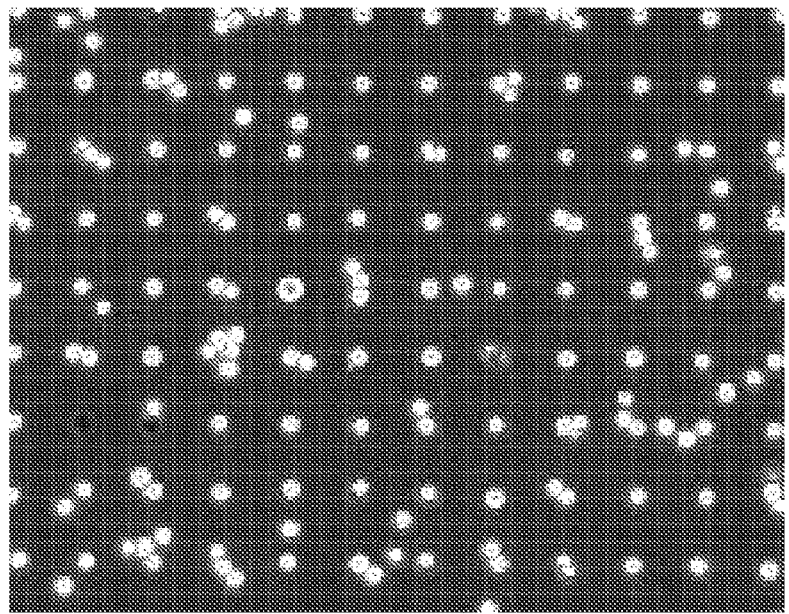
FIG. 9

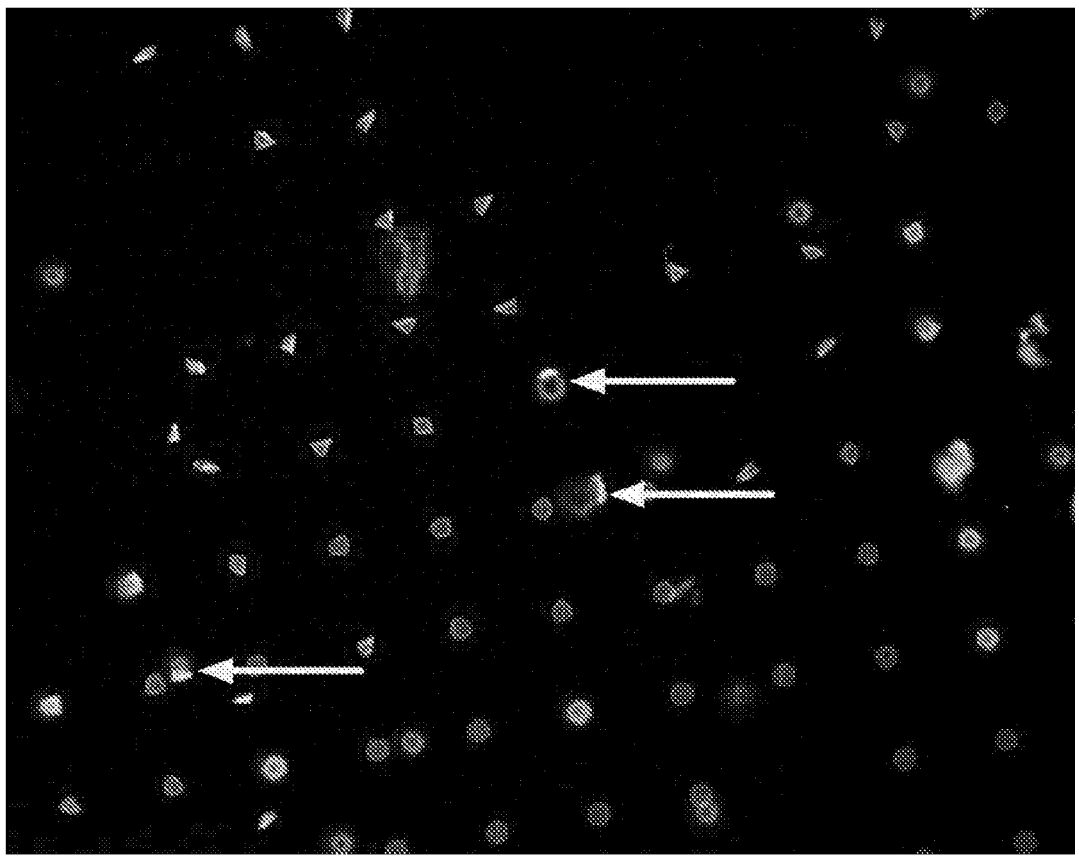
FIG. 10
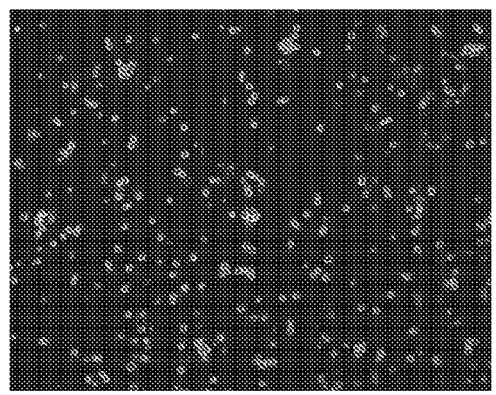 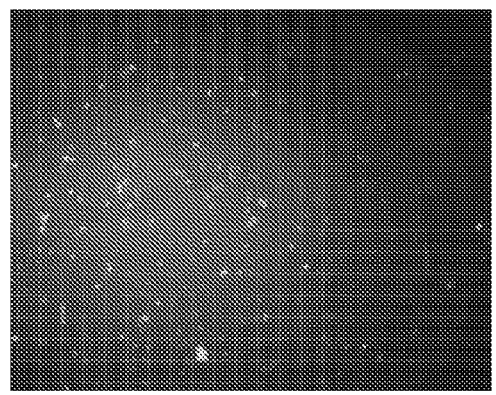
FIG. 11A  FIG. 11B

SYNTHETICALLY FUNCTIONALIZED LIVING CELLS

CLAIM OF PRIORITY

This application claims priority to provisional U.S. Patent Application No. 61/043,592, filed Apr. 9, 2008, which is incorporated by reference in its entirety.

FEDERALLY SPONSORED RESEARCH OR DEVELOPMENT

This invention was made with government support under contract number DMR 0213282 awarded by the National Science Foundation. The government has certain rights in the invention.

TECHNICAL FIELD

This invention relates to synthetically functionalized living cells.

BACKGROUND

Polyelectrolyte multilayers can be easily assembled on a variety of surfaces. Selection of the materials, assembly conditions, and post-processing conditions can be used to control the chemical, biological, structural and optical properties of the final product. Polyelectrolyte multilayers have previously been used in several biological applications, including drug delivery, biomaterial coatings, and precisely functionalizing surfaces to control adherent cellular growth.

SUMMARY

Polymer discs or bodies, or "patches," can be deposited onto the surface of a living cell, and this patch may serve as a broad platform to affect cellular behavior and functionality. These patches can be used to confer non-native functions and characteristics (including, for example, chemical, enzymatic, fluorescent, magnetic, or other characteristics) to the cell, while allowing the cell to perform its natural functions as well, since the patch covers only a portion of the cell surface.

A large number of patches can be fabricated over a large area (e.g., approximately 1 in$^2$ or larger) of a substrate simultaneously (using, e.g., lithographic techniques, though fabrication is not limited to lithography). Patches can be readily prepared using techniques for forming polyelectrolyte multilayers (PEMs). As fabricated on the substrate, each patch includes a labile layer that can dissociate under precisely selected conditions to release the layer(s) above (for example, which can include layers having affinity for cells and selected "payload" layers, which can include materials such as drugs or nanoparticles) from the substrate. Advantageously, the labile layer can undergo dissociation in the same solution (pH, salt concentration, etc.) and temperature conditions used to contact the cells to the patches. Thus, patch attachment to cells and patch dissociation from the substrate can occur in a single step.

In one aspect, a composition includes a cell, and a polymer patch associated with a fractional portion of the cell surface, where the polymer patch includes a cytophilic face having a specific affinity for the cell surface and being substantially in contact with the cell surface, and an exposed face.

The polymer patch can further include a functional layer intermediate to the cytophilic face and the exposed face. The functional layer can include a fluorescent material, a magnetic material, or a drug. The cytophilic face can include hyaluronic acid, chitosan, biotin, or an adhesive peptide. The cytophilic face can include a polyelectrolyte multilayer. The exposed face can include a polyelectrolyte multilayer. The polymer patch can have lateral dimensions in the range of 1 μm to 250 μm and a thickness in the range of 50 nm to 1 μm.

In another aspect, a polymer structure arranged on a substrate includes a substrate-adhering layer, a labile layer configured to selectively dissociate under predetermined conditions arranged over the substrate-adhering layer, and a cytophilic layer arranged over the labile layer, the cytophilic layer having a specific affinity for a surface of a predetermined cell type, where the cytophilic layer has a surface area smaller than a cell of the predetermined cell type.

The structure can include a diffusion barrier layer arranged intermediate to the labile layer and the cytophilic layer. The structure can include a functional layer arranged intermediate to the labile layer and the cytophilic layer. The substrate-adhering layer can include a polyelectrolyte multilayer. The substrate-adhering layer can include a polyelectrolyte multilayer. The labile layer can include a hydrogen-bonded polymer multilayer. The cytophilic layer can include a polyelectrolyte multilayer.

In another aspect, a polymer structure arranged on a substrate includes a substrate-adhering layer including a polyelectrolyte multilayer, a labile layer including a hydrogen-bonded polymer multilayer arranged over the substrate-adhering layer, and a cytophilic layer including a polyelectrolyte multilayer arranged over the labile layer, the cytophilic layer having a specific affinity for a surface of a predetermined cell type, and where the cytophilic layer has a surface area smaller than a cell of the predetermined cell type.

The structure can include a diffusion barrier layer including a polyelectrolyte multilayer arranged intermediate to the labile layer and the cytophilic layer; or a functional layer including a polyelectrolyte multilayer arranged intermediate to the labile layer and the cytophilic layer The cytophilic layer can include a ligand for a cell surface receptor of the predetermined cell type. The labile layer can be configured to dissolve under conditions conducive to binding of the cell to the cytophilic layer. The structure can be a member of a population of substantially identical polymer structures arranged on a substrate.

The structure can have lateral dimensions in the range of 1 μm to 250 μm and a thickness in the range of 50 nm to 1 μm. The structure can have lateral dimensions in the range of 1 μm to 100 μm. The structure can have lateral dimensions in the range of 1 μm to 50 μm.

In another aspect, a method of making a composition includes forming a polymer structure arranged on a substrate, the polymer structure including: a substrate-adhering layer including a polyelectrolyte multilayer, a labile layer including a hydrogen-bonded polymer multilayer arranged over the substrate-adhering layer, and a cytophilic layer including a polyelectrolyte multilayer arranged over the labile layer, the cytophilic layer having a specific affinity for a surface of a predetermined cell type, where the cytophilic layer has a surface area smaller than a cell of the predetermined cell type, and contacting the polymer structure with a cell of the predetermined cell type, thereby forming a cell-patch-substrate association, and causing the labile layer to release a cell-patch association from the substrate.

Contacting the polymer structure with a cell of the predetermined cell type can occur under conditions in which the labile layer is substantially soluble. The polymer structure can further include a diffusion barrier layer including a polyelectrolyte multilayer arranged intermediate to the labile layer and the cytophilic layer. The polymer structure can further include a functional layer including a polyelectrolyte multilayer arranged intermediate to the labile layer and the cytophilic layer. The cytophilic layer includes a ligand for a cell surface receptor of the predetermined cell type. The structure can be a member of a population of substantially identical polymer structures arranged on a substrate.

Causing the labile layer to release a cell-patch association from the substrate can include dissociating the labile layer. Dissociation can include, for example, dissolving hydrogen-bonded films, mechanical stress, and temperature induced dissolution, or a combination thereof. Contacting the polymer structure with a cell of the predetermined cell type can occur before, simultaneously with, or after causing the labile layer to release a cell-patch association from the substrate.

In another aspect, a method of attaching a layer to a surface of a cell includes exposing a cell to a polymer structure having a cytophilic layer, and releasing a portion of the polymer structure to expose the layer.

The details of one or more embodiments are set forth in the accompanying drawings and the description below. Other features, objects, and advantages will be apparent from the description and drawings, and from the claims.

BRIEF DESCRIPTION OF THE DRAWINGS

FIGS. 8A-8B are fluorescence micrographs of patches.
FIG. 9 is a micrograph showing cells attached to patches.
FIG. 10 is a micrograph showing cells attached to patches.
FIGS. 11A-11B are micrographs of cells attached to patches.

DETAILED DESCRIPTION

Figure 1A:
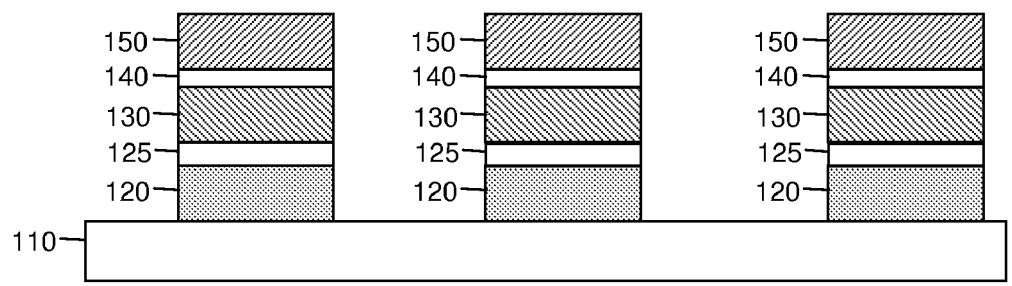
FIGS. 1A-1C are schematic depictions of patches and their associations with cells.

Synthetic materials have been interfaced with biological systems for cellular encapsulation applications. Since at least 1964, encapsulation strategies for cellular cargoes have focused on wrapping a cell or cell aggregate in a protective polymer shell to prevent an autoimmune reaction from deactivating the payload, while allowing small species through the encapsulating semipermeable membrane (see, e.g., Thomas M. S. Chang, *Science* 146 (3643), 524 (1964), which is incorporated by reference in its entirety). Many cell-based therapies, such as those that encapsulate islets cells for diabetes therapy, prefer this immunoisolation approach to systemic immunosupression. See, for example, Gorka Orive, et al., *Nat Med* 9 (1), 104 (2003); Hasan Uludag, et al., *Advanced Drug Delivery Reviews* 42 (1-2), 29 (2000); and Surita R. Bhatia, et al., *Current Opinion in Colloid & Interface Science* 10 (1-2), 45 (2005), each of which is incorporated by reference in its entirety.

Research on polyelectrolyte multilayer encapsulation has primarily focused on uniformly coating the surface of approximately spherical bodies, e.g., living or fixed cells. However, the approaches used restricted the accessibility of the cellular surface to the environment. An approach by which functionality is introduced to a relatively small fraction of a cellular surface (i.e., a "patch") can allow the majority of the cellular surface to remain free to interact with the environment.

Cellular encapsulation strategies have typically completely occluded the surface of the cell from direct contact with its environment. Past efforts have included using polymer multilayer assemblies on the surface of living and dead, fixed cells. See, for example, Matthieu Germain, et al., *Biosensors and Bioelectronics* 21 (8), 1566 (2006); A. Diaspro, et al., *Langmuir* 18 (13), 5047 (2002); S. Krol, et al., *Langmuir* 21 (2), 705 (2005); A. L. Hillberg and M. Tabrizian, *Biomacromolecules* 7 (10), 2742 (2006); S. Moya, et al., *Colloids and Surfaces A: Physicochemical and Engineering Aspects* 183-185, 27 (2001); and R. Georgieva, et al., *Langmuir* 20 (5), 1895 (2004), each of which is incorporated by reference in its entirety.

For cells that elute a species of interest (for example, a metabolite) that can diffuse through a protective membrane, encapsulation may be acceptable. However, for cells that require direct environmental contact to perform their desired functions, these encapsulation strategies can limit the usefulness of such cells. For example, the burgeoning fields of immune system engineering, adoptive T-cell therapies, and advanced cell-based vaccines realize little benefit from the traditional encapsulation paradigm.

Cellular passivation is only one possible option for useful cellular functionalization. For instance, by covering only a portion of a cellular membrane with a functional "patch," cell surface receptors on the rest of the cell membrane can remain free to interact with the environment. For example, poly(diacetylene)-conjugated liposomes can be attached to the cell surface, but many randomly attached nanometer sized "patches" were formed. See, for example, Sofiya Kolusheva, et al., *Angewandte Chemie International Edition* 44 (7), 1092 (2005), which is incorporated by reference in its entirety.

Uniform, multi-functional polymer patches can be attached to cells, and the patches subsequently released from an underlying substrate when exposed to physiological pH conditions and cell-compatible temperatures (e.g., between 4° C. and 37° C.). These engineered heterostructures can include both a "payload" component (such as, for example, superparamagnetic nanoparticles) and a cell-adhesive face that includes a component that has an affinity for the cells in question. For example, in the case of lymphocytes, the cell-adhesive face can include hyaluronic acid. For other cell types, cell-type specific antibodies can be employed to attach the patch to the membrane. The cells can attach to the patch before the patch releases from the surface, thus yielding a synthetically functionalized and living cell. The patches are also referred to as "backpacks," as they share certain characteristics with ordinary backpacks, such as portability, the ability to carry any desired cargo, and can be borne without impairing the functioning of the wearer.

One method to create the desired patch is with a polyelectrolyte multilayer. In some circumstances, polyelectrolyte multilayers can also confer desirable optical properties to surfaces, such as anti-reflectivity, or reflectivity in a desired range of wavelengths (see, for example, U.S. Patent Application Publication Nos. 2003/0215626 and 2006/0029634), and/or desirable surface energy characteristics. See, for example, U.S. Patent Application Publication Nos. 2006/0029634, which is incorporated by reference in its entirety.

A polyelectrolyte has a backbone with a plurality of charged functional groups attached to the backbone. A polyelectrolyte can be polycationic or polyanionic. A polycation has a backbone with a plurality of positively charged functional groups attached to the backbone, for example poly (allylamine hydrochloride) (PAH). A polyanion has a backbone with a plurality of negatively charged functional groups attached to the backbone, such as sulfonated polystyrene (SPS) or poly(acrylic acid) (PAA), or a salt thereof. Some polyelectrolytes can lose their charge (i.e., become electrically neutral) depending on conditions such as pH. Some polyelectrolytes, such as copolymers, can include both polycationic segments and polyanionic segments.

Layer-by-layer processing of polyelectrolyte multilayers can be used to make conformal thin film coatings with molecular level control over film thickness and chemistry. Charged polyelectrolytes can be assembled in a layer-by-layer fashion. In other words, positively- and negatively-charged polyelectrolytes can be alternately deposited on a substrate. One method of depositing the polyelectrolytes is to contact the substrate with an aqueous solution of polyelectrolyte at an appropriate pH. The pH can be chosen such that the polyelectrolyte is partially or weakly charged, or such that the polyelectrolyte is substantially completely or strongly charged. The multilayer can be described by the number of bilayers it includes, a bilayer resulting from the sequential application of oppositely charged polyelectrolytes. For example, a multilayer having the sequence of layers PAH-PAA-PAH-PAA-PAH-PAA would be said to be made of three bilayers. Each cycle of complimentary polymers produces a complexed, interpenetrated structure referred to as a "bilayer" and the following notation is commonly used: $(Poly_1X/Poly_2Y)_n$. Here, $Poly_1$ and $Poly_2$ refer to the abbreviation for the specific polymers or nanoparticles used in a selected assembly process, X and Y refer to the pH of the solution, and n is the number of bilayers that have been deposited. In some cases, n may be expressed in a decimal notation, such as for example, 3.5, which would indicate that three bilayers of $Poly_1X/Poly_2Y$ were deposited before a final "half-bilayer" of $Poly_1X$ was deposited. In some circumstances, charged nanoparticles can be used to as one or both of the charged species. See, for example, Lee, D., et al., *Nano Letters*, 6, 2305 (2006), which is incorporated by reference in its entirety.

The properties of weakly charged polyelectrolytes can be precisely controlled by changes in pH. See, for example, G. Decher, Science 1997, 277, 1232; Mendelsohn et al., Langmuir 2000, 16, 5017; Fery et al., Langmuir 2001, 17, 3779; Shiratori et al., Macromolecules 2000, 33, 4213; and U.S. patent application Ser. No. 10/393,360, each of which is incorporated by reference in its entirety. A coating of this type can be applied to any surface amenable to the water based layer-by-layer (LbL) adsorption process used to construct these polyelectrolyte multilayers. Because the water based process can deposit polyelectrolytes wherever the aqueous solution contacts a surface, even the inside surfaces of objects having a complex topology can be coated. In general, a polyelectrolyte can be applied to a surface by any method amenable to applying an aqueous solution to a surface, such as dipping or spraying.

Other modifications of a deposited polyelectrolyte multilayer are possible. For example, a nonporous polyelectrolyte multilayer can form porous thin film structures induced by a simple acidic, aqueous process. Tuning of this pore forming process, for example, by the manipulation of such parameters as salt content (ionic strength), temperature, or surfactant chemistry, can lead to the creation of micropores, nanopores, or a combination thereof. A nanopore has a diameter of less than 150 nm, for example, between 1 and 120 nm or between 10 and 100 nm. A nanopore can have diameter of less than 100 nm. A micropore has a diameter of greater than 150 nm, typically greater than 200 nm. Selection of pore forming conditions can provide control over the porosity of the coating. For example, the coating can be a nanoporous coating, substantially free of micropores. Alternatively, the coating can be a microporous coating having an average pore diameters of greater than 200 nm, such as 250 nm, 500 nm, 1 micron, 2 microns, 5 microns, 10 microns, or larger.

Desired chemistries can be included in the polyelectrolyte multilayers. The chemistry can be added during manufacture of the multilayer, or after manufacture. For example, antibacterial chemistries (such as silver nanoparticles or quaternary ammonium salts) can be included in the multilayer during manufacture. The resulting multilayer can then have desired properties (such as antibacterial properties) arising from the incorporated chemistry. In some circumstances, the chemistry can be controllably released from the multilayer.

A patch can be fabricated and functionalized ex vivo. In other words, the patch can be prepared in an environment substantially free of cells. An ex vivo approach can offer more opportunities in geometry, functionalization chemistries, and solvent conditions than does in vivo fabrication.

In general, a patch can have a multilayer structure. Typically the patch is fabricated on a substrate before being introduced to cells. The substrate or patch can optionally include an adhesion layer, depending on the substrate, selected to provide desired mechanical robustness to the patch on the substrate. The next layer is a labile releasable layer. The labile layer is composed of non-cytotoxic polymers. The labile layer can include polymers that dissociate in neutral pH conditions, such as H-bonded multilayer films, biopolymers digested by specific enzymes (such as cellulase digestion of cellulose derivatives), hydrolysable polymers, or polymer systems with temperature-dependant solubility (lower critical solution temperature, "LCST", behavior in particular).

H-bonded multilayer films can include polymers such as poly (acrylic acid) (PAA), poly(methylacrylic acid) (PMAA), poly (ethylene glycol) (PEG), poly(vinylpyrrolidone) (PVPON), poly(N-vinylcaprolactam) (PVCL), and poly(N-isopropylacrylamide) (PNIPAAm). The films can include but are not limited to PAA/PEG, PMAA/PEG, PMAA/PVPON, PMAA/PVCL, or PMAA/PNIPAAm films. In general, the labile layer is selectively removable, under controllable conditions, such that the remaining layers of the patch (described below) are released from the substrate.

The patch can include an optional diffusion barrier, depending on the diffusion characteristics of the functional layer (if present) and of the cytophilic layer. The cytophilic layer includes at least one polymer or other component that has a strong affinity to attach to a cell surface. For example, the cytophilic layer can include extracellular matrix (ECM) polymers (such as hyaluronic acid), or polymers functionalized with adhesive moieties, such as biotin, or adhesive peptides, such as antibodies or RGD-containing peptides. The materials and properties of the cytophilic layer can be chosen to favor attachment of the patch to a desired type of cell. For example, antibodies present in the cytophilic layer can promote attachment of cells bearing the corresponding antigen over cells that do not present the antigen. The cytophilic layer can include reactive groups capable of forming covalent bonds with functional groups on the cell surface. Cell-patch interactions are further discussed below.

A multilayer patch can be fabricated on a planar surface. Next, cells are introduced, and attach to the outermost cytophilic layer. Last, the labile layer is caused to dissolve or dissociate, an event that can be tuned depending on the nature of the diffusion barrier layer (such as thickness and pH assembly conditions) and environmental conditions such as salinity and temperature. The cells are thus freed from the surface, departing with a polymeric patch attached to its surface. In other words, the cell is partially encapsulated by the patch—only a fraction of the cell surface is covered by the patch. A schematic of this approach is illustrated in FIGS. 1A-1C.

In a modified approach, the patch can be fabricated on a planar surface. The labile layer is next caused to dissolve or dissociate, allowing the patches to float freely. In this free floating state, the patches can be exposed to and become attached to cells.

Figure 1B:
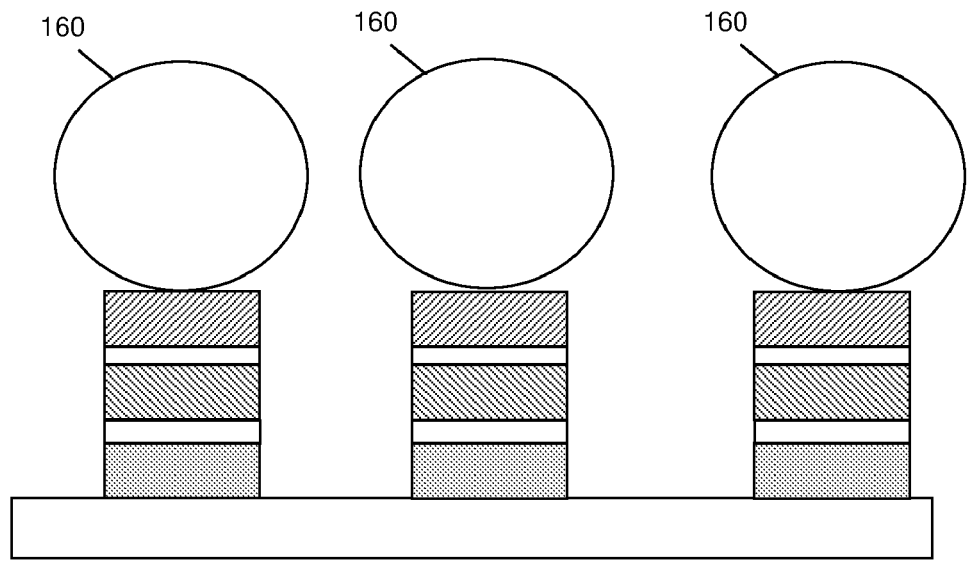
Figure 1C:
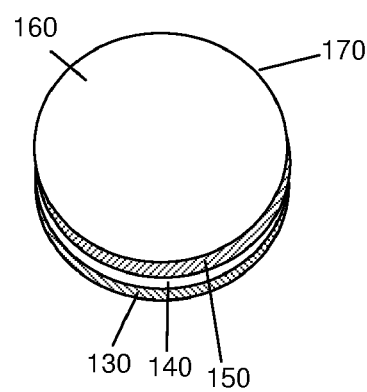
Figure 1D:
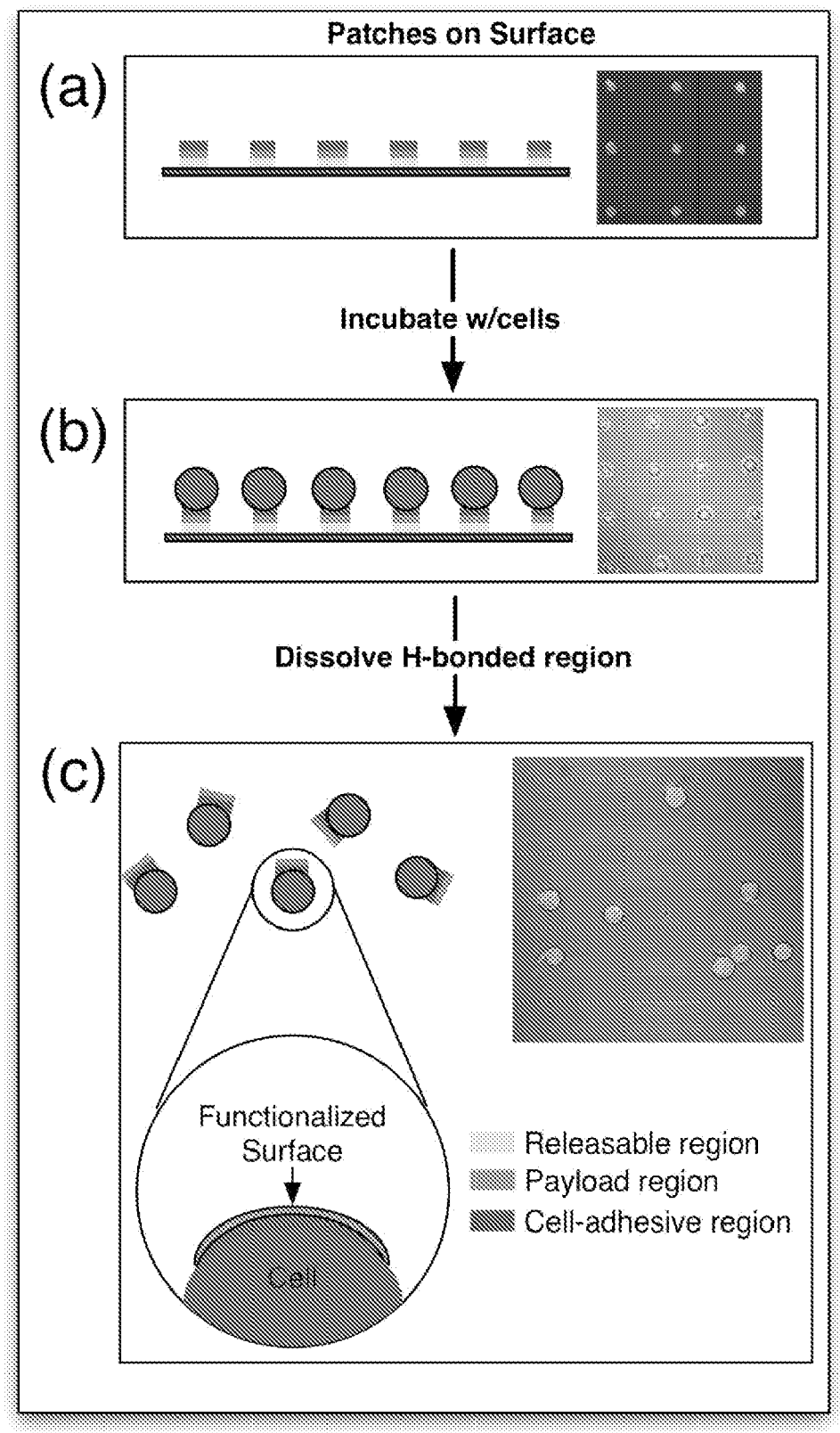
FIG. 1D is an overview of the cell functionalization scheme. Panel (a) shows a regular array of surface-bound patches spaced 50 µm apart. The green fluorescence is from FITC-PAH. Panel (b) shows that after cell incubation and attachment, a majority of the surface-bound patches are occupied. Panel (c) shows that the patches were released from the surface while remaining attached to the cell membrane.

FIGS. 1A-1D illustrate the fabrication of a patch on a substrate, its interaction with a cell, and release of the patch and associated cell from the substrate. Arranged on substrate 110 are three patches, each including an adhesion layer 120, labile layer 125, optional diffusion barrier 130, optional functional layer 140, and cytophilic layer 150. In FIG. 1B, cells 160 are exposed to the patches and individual cells become associated with individual patches via cytophilic layers 150. FIG. 1C illustrates a released cell following dissolution of the labile layer 125. Partially encapsulated cell 160 includes a portion of its surface associated with cytophilic layer 150, optional functional layer 140, and diffusion barrier 130. FIG. 1D presents another overview of cell functionalization with patches.

One method of forming patches is to prepare the desired multilayer assembly on a patterned "stamp," and then transfer this through a process known as polymer-on-polymer stamping, or POPS. POPS is an extension of microcontact printing, which requires the fabrication of a poly(dimethylsiloxane) (PDMS) stamp on which an "ink" is deposited. Inks used in microcontact printing have included small molecules, such as alkanethiols and alkylsiloxanes, as well as higher molecular weight polymers such as PAH. See, for example, Y. Xia, and G. M. Whitesides, J. Am. Chem. Soc. 117, 3274 (1995); Y. Xia, et al., J. Am. Chem. Soc. 117, 9576 (1995); and M. C. Berg, et al., Langmuir 19, 2231 (2003), each of which is incorporated by reference in its entirety.

POPS uses an ink that is an assembled PEM—that is, a PEM is built on the patterned PDMS stamp (see, e.g., P. T. H. J. Park, Advanced Materials 16, 520 (2004), which is incorporated by reference in its entirety). The stamp is brought into contact with a substrate selected for its ability to interact with the ink. For example, a gold substrate can be used when microcontact printing a thiol-based ink; or a planar substrate coated with another charged polymer in POPS. Specific interactions between the molecules on the PDMS and the substrate will encourage the liftoff of the ink in a complimentary pattern to the relief pattern on the PDMS stamp.

The POPS procedure can be sensitive to aspect ratios of the film thickness and feature diameter. For instance, a film 5 nm thick can easily be stamped with features of approximately 1 μm in size, but a film with a thickness of 50 nm can transfer more effectively if the features are approximately 10 μm in size.

Figure 2:
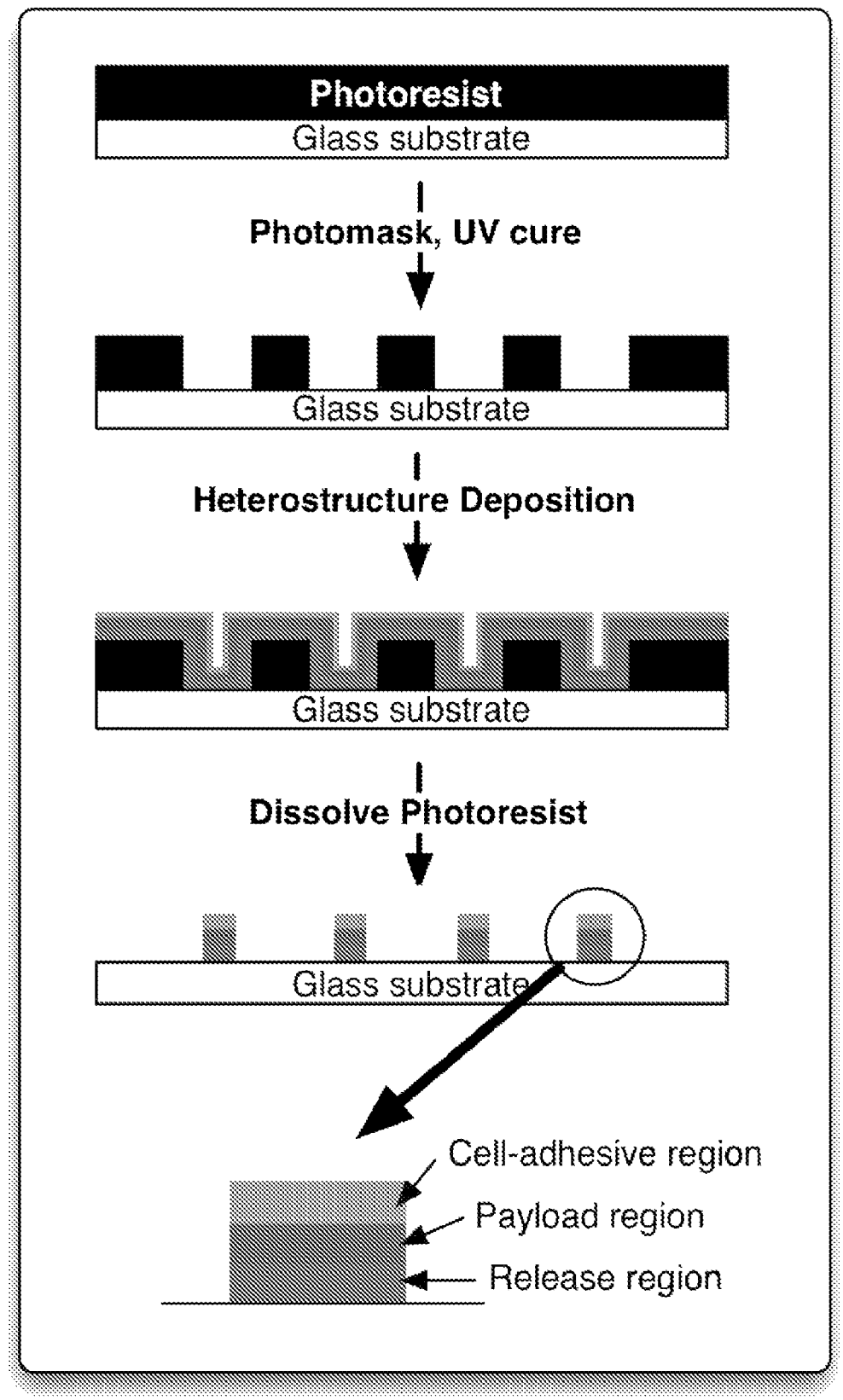
FIG. 2 is a schematic diagram of a method of making patches.

Another method of patch fabrication is a lithographic "lift-off" method. This method works with silica nanoparticle assemblies and some biopolymer systems. See, for example, F. Hua, et al., Langmuir 18, 6712 (2002); J. ShaikhMohammed, et al., Biomacromolecules 5, 1745 (2004); and J. ShaikhMohammed, et al., Langmuir 22, 2738 (2006), which is incorporated by reference in its entirety. FIG. 2 illustrates the method schematically. First, a substrate is uniformly coated with a positive photoresist (such as, for example Rohm&Haas S1813). A patterned photomask (e.g., Cr on glass) is placed above the photoresist, and the photoresist is UV cured in the pattern of the mask. For patch fabrication, the selected pattern can be, for example, 1-20 μm wells in the photoresist layer, although any pattern compatible with the photolithographic method is possible. Next, a multilayer is deposited atop of the patterned resist with the following exemplary composition: (adhesion layer)$_5$ (labile layer)$_x$ (PEM functional layer)(cytophilic layer)$_y$. The last lithographic step is to dissolve the photoresist in an organic solvent such as N-methylpyrrolidone (NMP) or acetone, leaving only the polymer posts that adsorbed directly to the substrate (see, e.g., FIG. 2). The use of sonication during the photoresist dissolution step can be important for desired fabrication, due to the continuity of the film over the photoresist islands. Finally, cells can incubated atop the posts, and attach to the cytophilic layer. Next, dissociation of the labile layer is triggered, either by appropriate pH or temperature conditions.

Deposition of the cytophilic biofilm directly over the labile layer can in some circumstances render the labile layer insoluble in phosphate buffered saline (PBS) (and thus unable to undergo the desired dissolution). The following film composition, including Poly(acrylamide) (PAAm), PAA, hyaluronic acid (HA), and chitosan (CHI), was considered: (PAAm/PAA)$_{10.5}$(HA/CHI)$_{3.5}$. The PAAm/PAA layer has been observed to dissolve almost instantly when exposed to Milli-Q water (pH approximately 5.5), but was insoluble (in Milli-Q or PBS) when the HA/CHI layer was deposited on top. This may be due to the electrostatic and hydrogen-bonding capabilities (due to numerous hydroxyl groups along the polysaccharide) of hyaluronic acid and chitosan. See, e.g., L. Richert et al., Langmuir 20, 448 (2004), which is incorporated by reference in its entirety. Diffusion of the hyaluronic acid and chitosan into the H-bonded layer may crosslink and stabilize the release layer.

A PEM film that diffuses to only a small extent (i.e., a diffusion barrier layer) including fully charged polyelectrolytes can inhibit this possible diffusion process. Lavalle and co-workers systematically probed the diffusion inhibiting behavior of (PAH/SPS) layers within (HA/poly(L-lysine)) films (see, e.g., J. M. Garza et al., *Langmuir* 20, 7298 (2004), which is incorporated by reference in its entirety). As few as 2 bilayers of PAH/SPS were sufficient to completely eliminate the diffusion of poly(lysine) between multilayer compartments (see, for example, F. Boulmedais, et al., *Langmuir* 19, 9873 (2003), which is incorporated by reference in its entirety). For example, a (PAH3/SPS3) (two fully-charged polymers under the pH conditions used) layer between the cytophilic layer and the releasable H-bond layer, can be used as a diffusion barrier layer. The relevant feature of the diffusion barrier layer is that the polyelectrolytes in the layer are substantially fully charged.

Figure 3:
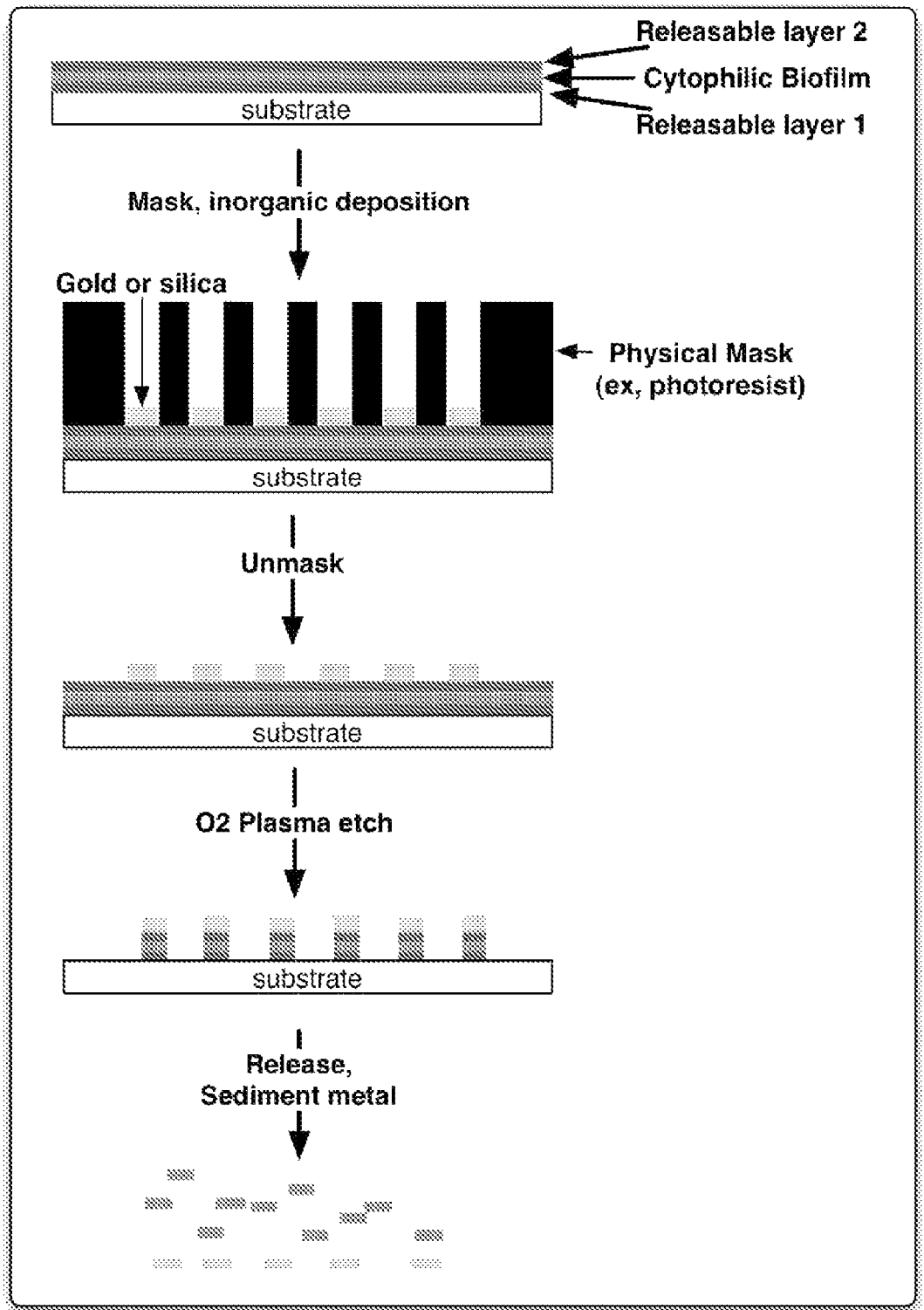
FIG. 3 is a schematic diagram of a method of making patches.

A third method of fabricating patches is a lithographic plasma-etching method. FIG. 3 illustrates this method schematically. A 4-ply composite stack of multilayers on a planar substrate is first prepared. The first layer is an adhesion layer, which encourages strong adhesion and uniformity of subsequent stacks. The second stack is a labile layer, which will readily dissolve in neutral or buffered conditions (see, e.g., S. A. Sukhishvili, S. Granick, *Macromolecules* 35, 301 (2002); and J. Cho, F. Caruso, *Macromolecules* 36, 2845 (2003), each of which is incorporated by reference in its entirety). The cytophilic layer is third, followed by a final labile layer. One exemplary structure is: $(PAH4/SPS4)_{5.5}$ $(PAA3/PAAm3)_{20}$ $(HA3/PAH3)_{x.5}(PAAm3/PAA3)_{20}$.

The next step is to physically mask the multilayer with a porous structure that contains holes on the order of, for example, 1-20 μm, such as developed photoresist. Next, electron-beam or thermally evaporated gold or $SiO_2$ can be deposited onto the surface of the outer labile layer, and form islands 1-20 μm in diameter. These metal islands act as a physical mask for the next step, an oxygen plasma etch (150 mTorr, 10 min) of the exposed film. Following the plasma etching step, all that remains are 4-ply posts of polymer multilayers, capped with a gold or $SiO_2$ island. The last step is to dissolve the releasable (PAAm/PAA) stacks by submerging in neutral pH water, sedimenting out the inorganic islands, and leaving the cytophilic layer suspended in solution.

The oxygen plasma method is an isotropic etch technique. Lateral removal (parallel with substrate surface) can occur beneath the metal masking. However, considering the aspect ratio of the mask to the thickness of the composite multilayer film, such lateral removal is unlikely to be significant. Data for the thickness of an exemplary system is shown in Table 1. If a 3 μm diameter metal island is deposited, the aspect ratio (diameter/height) is approximately 30. Even if the rate of lateral etching is equal to vertical removal, the size (i.e., diameter) of the final patch will not be significantly affected.

TABLE 1

| (PAH4/SPS4)5.5 | 12 nm |
| (PAA/PAAm-800k MW)10 | 63 nm |
| (HA3/FITC-PAH3)3.5 | 23 nm |
| Total thickness | 98 nm |

The fabrication methods discussed above can provide a polymer patch attached to a cellular surface, with only one face of the patch exposed to solution. Each side of the patch can present different chemical moities, resulting in a bifunctional polymer disc. For example, biotin can be incorporated into the strong PEM diffusion barrier during film growth, leaving the other face free to bind to CD44 receptors on the cell. Then, a myriad of streptavidin-conjugated molecules can be easily tagged to the cell in very limited and highly controlled domain sizes. See, e.g., J. M. Garza et al., *Langmuir* 20, 7298 (2004); and F. Boulmedais, et al., *Langmuir* 19, 9873 (2003), each of which is incorporated by reference in its entirety.

Another example of surface functionalization is to provide non-native abilities to the cells by virtue of the associated patches. In one example, during PEM fabrication, magnetic nanoparticles can be impregnated into the layers, and once the final polymer patch is attached to the surface of the cell, the cells responded to an applied magnetic field. Any number of functional materials, including (but not limited to) magnetic and environmentally-responsive materials, drugs, or imaging contrast agents, can be included in a patch. The corresponding function can thus be provided to cells.

An in vivo method can functionalize the surface of a living cell. A PEM film is stamped directly onto the cell surface without first fabricating a patch as described above. This can be accomplished by using a modified POPS protocol, similar to what has been used to fabricate Janus-style capsules (see, e.g., Z. Li, *Macromolecules* 38, 7876 (2005), which is incorporated by reference in its entirety. A cytophilic, HA-terminated PEM can be assembled on a patterned or unpatterned PDMS stamp. This PDMS stamp is then lowered onto a monolayer of adherent cells, either densely packed or ordered into a 2D periodic structure (see, e.g., H. Kim, *Advanced Functional Materials* 16, 1313 (2006), which is incorporated by reference in its entirety).

After PEM deposition onto the cell surface, well-established chemistries, such as EDC/NHS (1-ethyl-3-(3-dimethylaminopropyl) carbodiimide hydrochloride/N-hydroxy-succinimide), can be used to functionalize the PEM film in addition to any functionalization added during the PEM deposition process (that is, during PEM film fabrication).

Non-Polyelectrolyte or Hydrogen-Bonded Multilayer Based Patch Fabrication Techniques Other methods can fabricate a patch that will perform similarly or identically to patches made using layer-by-layer techniques. For instance, a heterostructured patch may be made by "inking" (e.g., non-selectively adsorbing to the surface) several regions of polymer onto a patterned PDMS stamp, and then transferring this pattern using polymer-on-polymer (POPS) techniques. Similarly, polymer layers can be applied from solutions using spin coating, dip coating, spray coating, surface grafting, vapor deposition, fluidized bed coating, roller coating, or meniscus coating, and may be patterned using a PDMS stamp with POPs techniques, a lithographically patterned substrate with selective liftoff, or a patterned barrier or mask. A key design criteria for any solution-based deposition technique is that the solvent system used to apply a given layer onto a previously applied layer must not substantially dissolve or disrupt the previous layer. For instance, a labile region of PNIPAAm homopolymer or other material with a chemically, thermally or mechanically triggered release capability may be applied to a surface from a water based solution, and a polymer functionalized with cell interacting moieties such as adhesion tripeptides like RGD can be applied to this previous layer from non-aqueous solutions. Suitable non-water soluble polymers include functionalized polyamides, polyesters, polyurethanes, acrylic copolymers, and methacrylic copolymers, and polysaccharides such as chitin, and cellulose, to name a few. Suitable water-soluble polymer solutions include PAA, PMAA, PVPON, PAH, poly (vinyl pyridine), poly(vinyl alcohol), PEG, PAAm, PDAC, SPS, and water soluble polysaccharides such as chitosan, carboxymethylcellulose, hyaluronic acid, dextran, and alginate, to name a few. Synthetic and natural derivatives of both the non-water soluble and water-soluble polymers may also be considered.

EXAMPLES

Bifunctional patches can be fabricated using a POPS technique. First, a PDMS stamp was made from a Si master (e.g., a Si wafer covered in a patterned SU-8 photoresist layer), and a composite polyelectrolyte multilayer/hydrogen-bonded multilayer stack built on top of it. This composite structure can generally include at least four distinct layers. The first was a monolayer of PAH, which uniformly coated the hydrophobic PDMS when deposited under specific basic conditions (i.e., 50 mM, pH=10.5, 100 mM NaCl). Next was the multilayered stack (in this case, containing cytophilic hyaluronic acid) that became the bifunctional patch that is attached to the cell. Next was a labile layer, e.g., prepared from a low MW polyacrylamide and polyacrylic acid, a system known to quickly degrade under neutral pH conditions (see, e.g., S. A. Sukhishvili, S. Granick, *Macromolecules* 35, 301 (2002), which is incorporated by reference in its entirety). Another structure for a labile layer is a multilayer of poly(vinyl pyridine) and poly(acrylic acid) (see, for example, J. Cho, F. Caruso, *Macromolecules* 36, 2845 (2003), which is incorporated by reference in its entirety). Using this same approach, Decher and co-workers have shown the release of a free-standing PEM sheet using the pH-dependant dissolution of a hydrogen-bonded sacrificial layer (S. S. Ono, G. Decher, *Nano Lett.* 6, 592 (2006), which is incorporated by reference in its entirety). The last stack was an adhesion layer that that rendered the composite stack uniformly charged (either cationic or anionic) at all pH conditions. This layer was then brought into contact with the substrate, and the last layer (i.e., the adhesion layer) was chosen to be of opposite charge from the stamping substrate to facilitate adhesion and lift-off.

Figure 4:
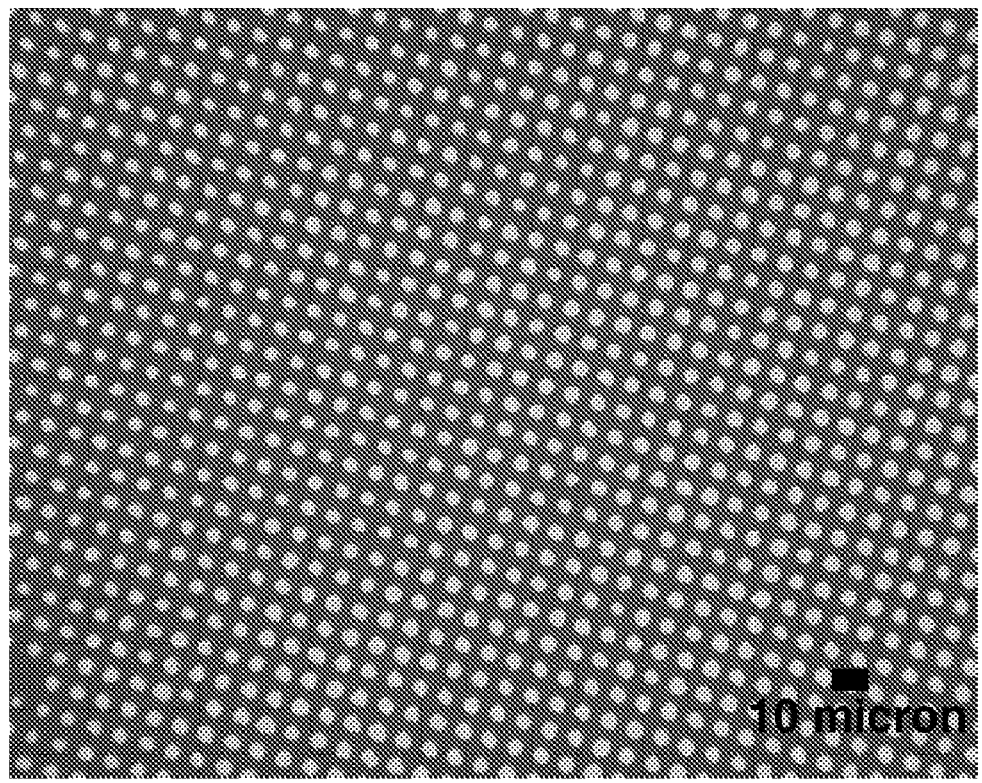
FIG. 4 is a fluorescence micrograph of patches.

A fluorescence microscope image of a composite multilayer stack prepared by POPS $(PAH10.5)_1(PAA3.5/FITC-PAH7.5)_3(PAAm3/PAA3)_{10}(PAH4/SPS4)_{10}$ on a cationic glass slide is depicted in FIG. 4. The first PEM deposited contained fluorescein (in the form of fluorescein-labeled poly (allylamine hydrochloride) (FITC-PAH)); thus, the fluorescence observed indicated complete transfer of the stack. The diameter of the posts was 5 μm. A cytophilic stack can have the structure $(PAH10.5)_1(HA7.5/PAH3.5)_x(PAAm3/PAA3)_{10}(PAH4/SPS4)_5$, where x indicates a variable number of bilayers.

Figure 5:
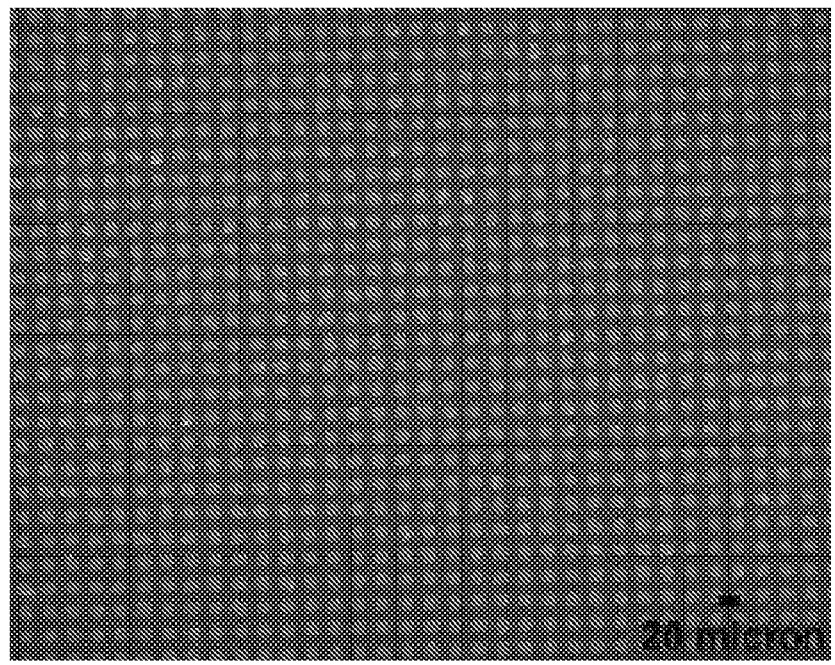
FIG. 5 is a fluorescence micrograph of patches.
Figure 6:
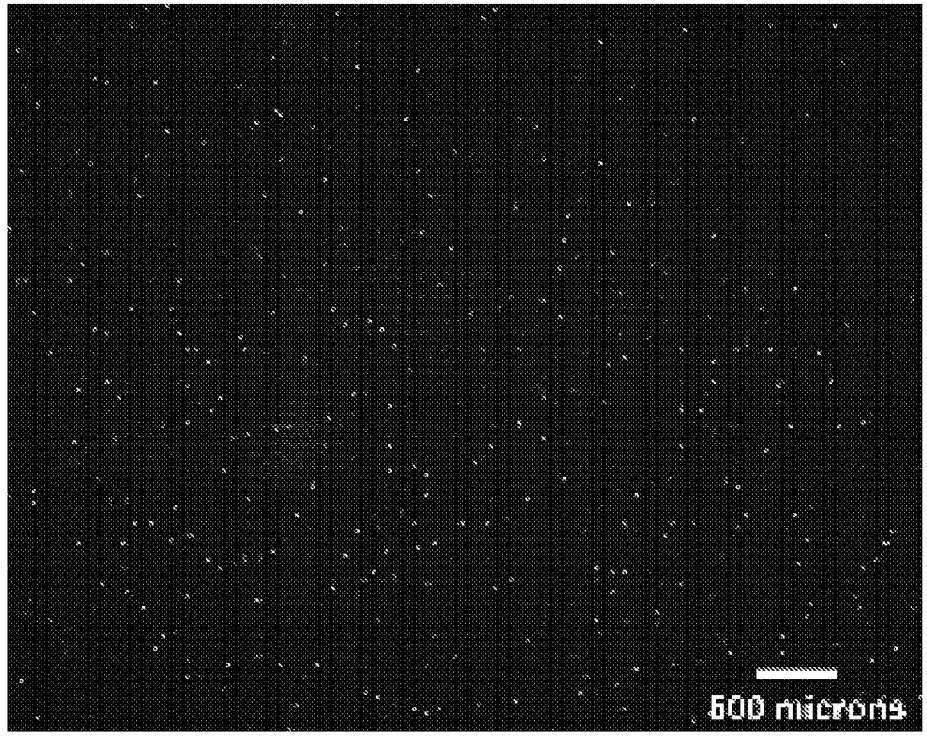
FIG. 6 is a fluorescence micrograph of beads interacting with patches.

A photolithographic lift off method was used to fabricate 3-ply polymer posts on a coated glass substrate The coating included poly(diallyldimethylammonium chloride) (PDAC) and poly(styrene sulfonate) (SPS), and had the structure $(PDAC4/SPS4)_{15.5}$. The posts included PAA and poly(4-vinylpyridine) had the formula $(PAA3/P4VP3)_{10.5}(CHI-FITC3/HA3)_{3.5}$. Fluorescence images of these posts are found in FIG. 5. High-fidelity posts were obtained over very large areas (approximately 1 in $^2$). The ability of oppositely charged spheres to attach to these cation-terminated posts was investigated, and a fluorescent image showing these spheres is found in FIG. 6. The spheres are carboxyl-functionalized polystyrene beads, 10±0.56 μm in diameter, that were suspended in solution (pH approximately 5.5) and incubated on top of the post-laden substrate shown in FIG. 5. There are two intensities of fluorescent signal—more intense dots are beads attached to the top of the post, and less intense dots are attached to the substrate beneath. It was found that the beads preferentially attached to the posts, despite the cation-terminated PEM $((PDAC/SPS)_{15.5})$ coating the substrate.

Figure 7A:
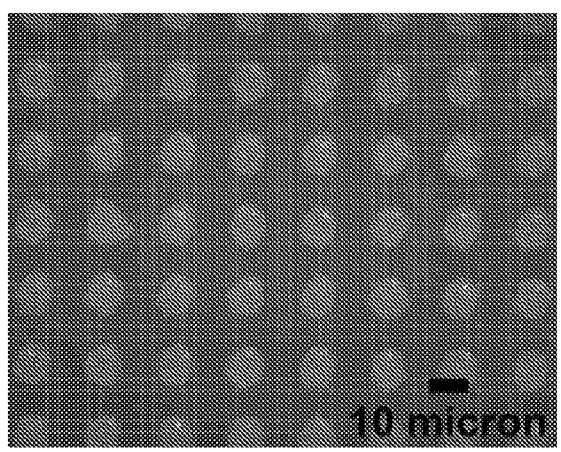
FIGS. 7A-7B are fluorescence micrographs of patches.
Figure 7B:
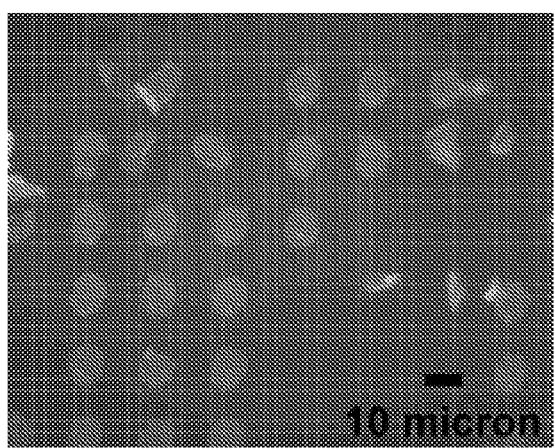

In a film that employed a diffusion barrier, exposure to PBS allowed dissociation of the H-bonded releasable layer. FIGS. 7A-7B are fluorescence micrographs of a field of 8 μm posts of $(PAA3/PEG3)_{10.5}(PAH3/SPS3)_{5.5}(HA3/FITC-CHI3)_{3.5}$, shown (A) immediately after acetone lift-off, and (B) following 15 minutes of exposure to PBS. As can be seen in FIG. 7B, some released patches rolled up or collapsed on themselves, whereas others re-deposited flatly onto the cationic substrate. This dissolution behavior was evidently limited to only approximately 10% of the total substrate area. Increasing the thickness of the labile layer can encourage H-bonded release of fully-charged PEM films built atop (PAA/PEG) (see, e.g., S. S. Ono, G. Decher, *Nano Lett.* 6, 592 (2006), which is incorporated by reference in its entirety).

Films using $(PAA/PEG)_{25.5}$ as the labile layer were fabricated, and allowed more than 50% patch lift-off in 15 minutes exposure to PBS at room temperature. FIGS. 8A-8B are fluorescence micrographs of a field of 20 μm posts consisting of a $(PAA/PEG)_{25.5}$ labile layer, diffusion barrier, and a FITC-labeled cytophilic layer, shown (A) immediately after acetone lift-off, and (B) following 15 minutes of exposure to PBS. The use of a diffusion layer can still be desirable, and the thickness of the labile layer required for liftoff can depend on the presence of a diffusion layer.

Interaction of polyelectrolyte multilayer-based patches with CH27 murine B-lymphocytes was investigated. These cells were chosen for their physiochemical similarity to e.g., human cytolytic T lymphocytes, but are more robust than human T cells and have been immortalized. B-lymphocytes are non-adherent cells that rarely agglomerate, which makes the design of cell-patch interaction schemes a unique challenge and opportunity.

Desirably, the interaction between the cell membrane and the cytophilic layer does not substantially alter the cell's native functions. Exemplary methods for encouraging the interaction of cells with a cytophilic layer include the interaction between lymphocyte cell-surface receptor CD44 and hyaluronic acid; the non-selective decoration of a cell's surface with biotin and streptavidin, paired with biotin on the surface of the patch; and covalent crosslinking between reactive functional groups on the patch and cell surface, either by direct reaction or by reaction of each separately with functional groups on a crosslinking reagent. More interaction mechanisms are possible, and are not limited to the ones mentioned above.

A PEM patch was fabricated according to the following formula: $(PDAC4/SPS4)_{15.5}(PAA/PEG)_{20.5}(PAH3/SPS3)_{9.5}(HA3/FITC-CHI)_{3.5}$. A brightfield image of the resulting B-cell array can be seen in FIG. 9. The diameter of each cell is approximately 20 μm.

Following the attachment of cells to the cytophilic layer of a patch, the patches were released from the surface. The following film composition was used: $(PAA/PEG)_{25.5}$ (FITC-PAH3/SPS3)$_{10}$(CHI3/HA3)$_3$. FIG. 10 shows an overlaid optical and fluorescent micrograph. The cells marked by yellow arrows are freely floating in solution (i.e., have been released from the surface), and were closely associated with the fluorescein-labeled PEM patch (as indicated by the green fluorescence).

Cell Adhesion by Stamping

A cytophilic, HA-terminated PEM was assembled on a PDMS stamp. The PDMS stamp was then lowered onto a monolayer of CH27 cells anchored to hyaluronic acid spin-coated glass slides. The cells then adhered to the HA-terminated PEM and delaminated a small "plug" from the film. FIGS. 11A-11B show optical micrographs of CH27 murine lymphocytes after 20 minutes of stamping with a (PAH7.5/

PAA3.5)10 (FITC-CHI/HA)5 multilayer: (A) brightfield image and (B) corresponding fluorescent image (due to the FITC-CHI containing PEM).

Superparamagnetic Patches

Materials. Poly(methylacrylic acid) (PMAA, Poly-Sciences, M=100 kDa), poly(acrylic acid) (PAA, Aldrich, M=450 kDa), poly(allylamine hydrochloride) (PAH, Aldrich, MW=70 kDa), poly(ethylene glycol) (20 kMW-PEG, Aldrich, M=20 kDa), poly(ethylene glycol) (1000 kMW-PEG, Aldrich, M=100 kDa), poly(N-isopropylacrylamide) (PNIPAAm, Polymer Source, M=258 kDa), fluorescein-labeled poly(allylamine hydrochloride) (FITC-PAH, Aldrich, M=70 kDa), poly(diallyldimethylammonium chloride) (PDAC, Aldrich, M=200-350 kDa in 20% aqueous solution), poly(styrene sulfonate) (SPS, Aldrich, M=70 kDa), hyaluronic acid (HA, from Strepococcus equi, Fluka, M approximately 145 kDa by intrinsic viscosity (see, e.g., R. Mendichi, et al., *Biomacromolecules* 4 (6), 1805 (2003), which is incorporated by reference in its entirety)), and low MW chitosan (CHI, DS=0.85, M approximately 390 kDa by intrinsic viscosity) were used without purification. RMPI with L-glutamine (Mediatech), Penicillin/Streptomycin (P/S, Mediatech), fetal calf serum (characterized FCS, Mediatech), HEPES (VWR Scientific), and $NaHCO_3$ (VWR Scientific) were used for cell culture media. Iron oxide magnetic nanoparticles ($Fe_3O_4$ NP, 10 nm diameter, Ferrotec EMG 705) stabilized with an anionic surfactant were used. Fluorescein-labeled chitosan was prepared according to the method of Tikhonov and Monfort (see Vladimir E. Tikhonov, et al., *Journal of Biochemical and Biophysical Methods* 60 (1), 29 (2004), which is incorporated by reference in its entirety) and stored in a desiccator. Cells were maintained and passaged in RPMI 1640 cell culture media supplemented with 10% FCS, 5 mL/L P/S solution, 25 mM HEPES, and 18 mM $NaHCO_3$.

Patterned multilayer heterostructure assemblies were prepared by a traditional lift-off photolithographic approach to pattern ultra-thin polymer films (see FIG. 2; see also J. ShaikhMohammed, et al., *Biomacromolecules* 5 (5), 1745 (2004); and J. ShaikhMohammed, et al., *Langmuir* 22 (6), 2738 (2006), each of which is incorporated by reference in its entirety). A positive photoresist was deposited onto a substrate, which is then exposed with a 365 nm UV light source through a chromium-on-glass mask patterned with 10 or 15 μm diameter holes. After development, the features in the photoresist extend down to the substrate. A heterostructured polymer multilayer film was deposited conformally on both the patterned photoresist and the exposed substrate. In the final step, the sample was sonicated in acetone to dissolve the photoresist and release the polymer film deposited on top. This procedure left only the polymer that had been deposited within the features and attached directly to the substrate. Using this approach, uniformly patterned, heterostructured, surface-bound patches could be made over areas as large as one square inch. This fabrication method can be used to fabricate patches over larger areas.

An aqueous-based layer-by-layer technique was used to deposit the functional, heterostructured polymer film. This technique has been used extensively for both polyelectrolyte and hydrogen-bonded films (see, e.g., S. S. Shiratori and M. F. Rubner, *Macromolecules* 33 (11), 4213 (2000); J. Choi and M. F. Rubner, *Macromolecules* 38 (1), 116 (2005); and Gero Decher, *Science* 277 (5330), 1232 (1997), each of which is incorporated by reference in its entirety).

Measurement of Patch Release Efficiency. Coordinate axes were drawn on substrates containing surface-bound patch arrays, which were photographed before exposure to neutral pH conditions. The substrates were submerged in PBS and gently agitated on an orbital shaker at 100 $min^{-1}$. Using the coordinate axes, identical regions were photographed before and after PBS exposure. These before-and-after micrographs were compared, and each patch was determined to have either not released (still on original lattice site) or released and readsorbed onto the glass substrate. The ratio of the number of non-released patches to the total number of patches counted before exposure was recorded. Each value was the average of at least three micrographs representing separate regions on the substrate, which typically included approximately 300 patches.

Measurement of Cell-Patch Interaction Efficiency. To test the binding efficiency of the cell-surface CD44 to (HA/CHI)-terminated patches, such patches were fabricated without a release region. B-cells in RPMI media (approximately $10^6$ cell/mL) were introduced on the surface, agitated on an orbital shaker (100 $min^{-1}$) for 15 minutes at room temperature, then incubated at 37° C. for 15 minutes. Some samples were agitated and incubated a second time. At least 4 brightfield images (surveying approximately 400 patches each) were analyzed for the number of patches occupied with one cell, with multiple cells, the number of empty patches, and the number of cells attached to 'interstitial' areas between patches.

Cell Functionalization. A patch-laden glass slide was cut and placed in the bottom of a well in a 6-well plate. 2 mL of B-lymphocytes suspended in RPMI media (approximately $10^6$ cells/mL) were pipetted onto the patch-laden surface. The entire plate was agitated for 15 minutes at 37° C., followed by 37° C. incubation for 15 minutes. This agitation/incubation cycle was repeated. Once on the surface of a patch, CD44 cell surface receptors anchor onto the HA within the cell-adhesive region. The glass slide, now containing lymphocytes attached to surface-bound patches, was removed and gently shaken for approximately 15 s upside down in 37° C. PBS to remove all cells not attached to a patch. The glass slide was returned to a new well containing 4° C. media, and the entire plate was chilled to 4° C. for 10 minutes. Confocal laser scanning microscopy (CLSM) was used to image cells decorated with a fluorescent polymer patch.

An adhesion layer, with formula $(PDAC4/SPS4)_{15.5}$ with a typical thickness of 55 nm, made the substrate uniformly and positively charged at all pH's and provides an adhesive surface for subsequent depositions (see, e.g., Z. Z. Wu et al., *Advanced Materials* 18 (20), 2699 (2006), which is incorporated by reference in its entirety). This region was preferably deposited prior to photoresist deposition and patterning, but it may also be deposited onto the developed photoresist without affecting patch fabrication.

The second region of the heterostructure was designed to deconstruct (e.g., to release layers above from layers below) readily upon exposure to physiological (or at least substantially non-cytotoxic) conditions. Several deconstruction mechanisms may be considered here, such as salt concentration, pH, or temperature (see, for example, D. M. Lynn, *Advanced Materials* 19 (23), 4118 (2007), which is incorporated by reference in its entirety). A hydrogen-bonded multilayer that deconstructs at physiological pH but not at physiological temperature was chosen. PMAA/PNIPAAm films dissolve above pH approximately 6.2, although other hydrogen-bonding polymer combinations with higher critical pH values may be used (see, e.g., Eugenia Kharlampieva and Svetlana A. Sukhishvili, *Polymer Reviews* 46 (4), 377 (2006), which is incorporated by reference in its entirety). The lower critical solution temperature (LCST) behavior of PNIPAAm affords further control over the release behavior—above the LCST temperature of 32° C., polymer-polymer segment interactions are favored over polymer-solvent interactions. In particular, polyanion/PNIPAAm films demonstrate this characteristic through temperature dependent diffusion behavior (see, for example, T. Serizawa, et al., *Macromolecules* 37 (17), 6531 (2004); and J. F. Quinn and F. Caruso, *Langmuir* 20 (1), 20 (2004), each of which is incorporated by reference in its entirety). The highly interdigitated nature of the multi-layered film does not allow the release region to dissolve above the LCST. When the temperature drops well below the LCST, (such as the commonly used 4° C. condition used in tissue culture work), the release region has both the pH and temperature conditions needed to deconstruct and release the patch.

Figure 20:
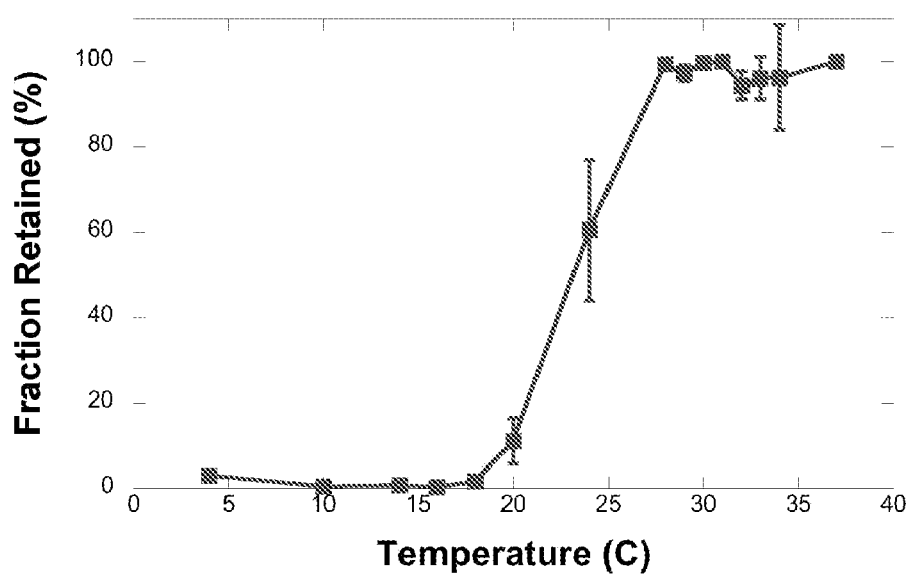
FIG. 20 is graph depicting thermal characteristics of a patch.
Figure 21:
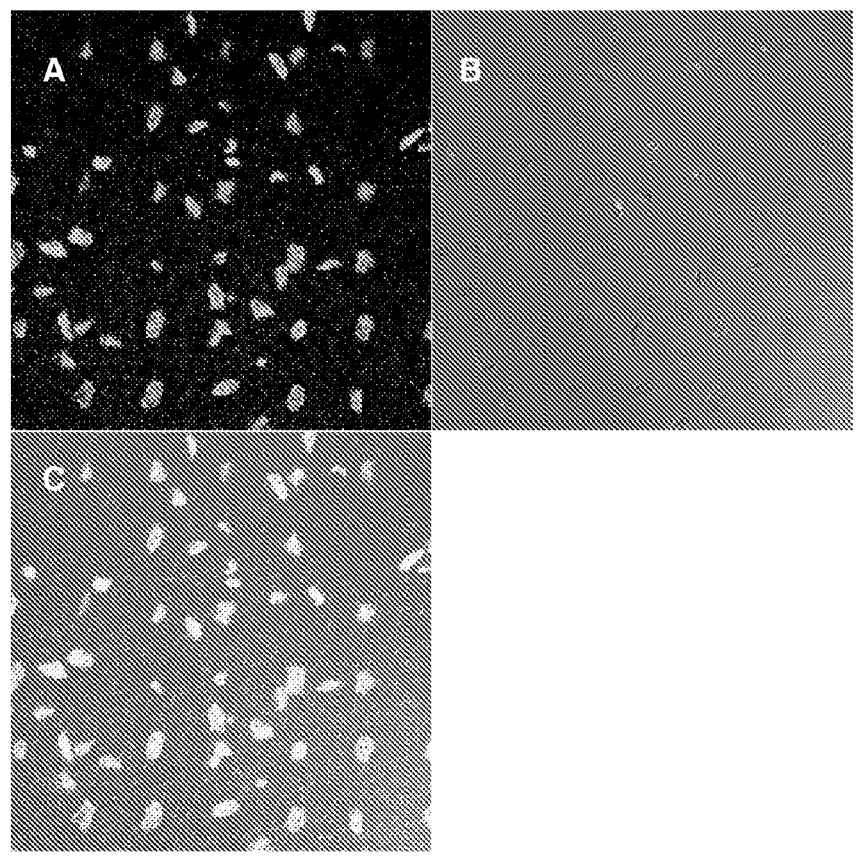
FIGS. 21A-21C are micrographs depicting patches.
Figure 22:
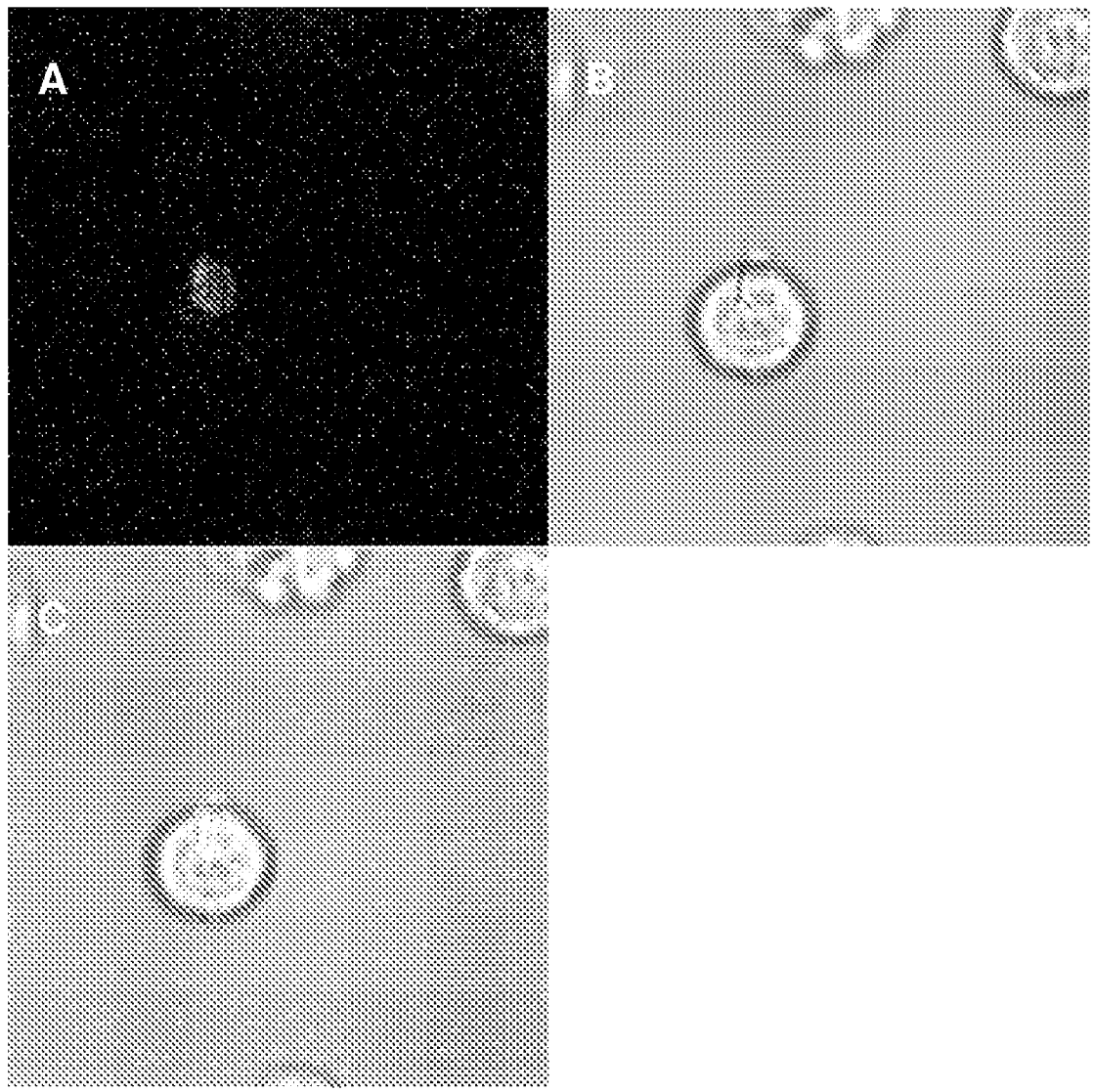
FIGS. 22A-22C are a group of images depicting a fluorescent patch associated with a single cell.
Figure 23:
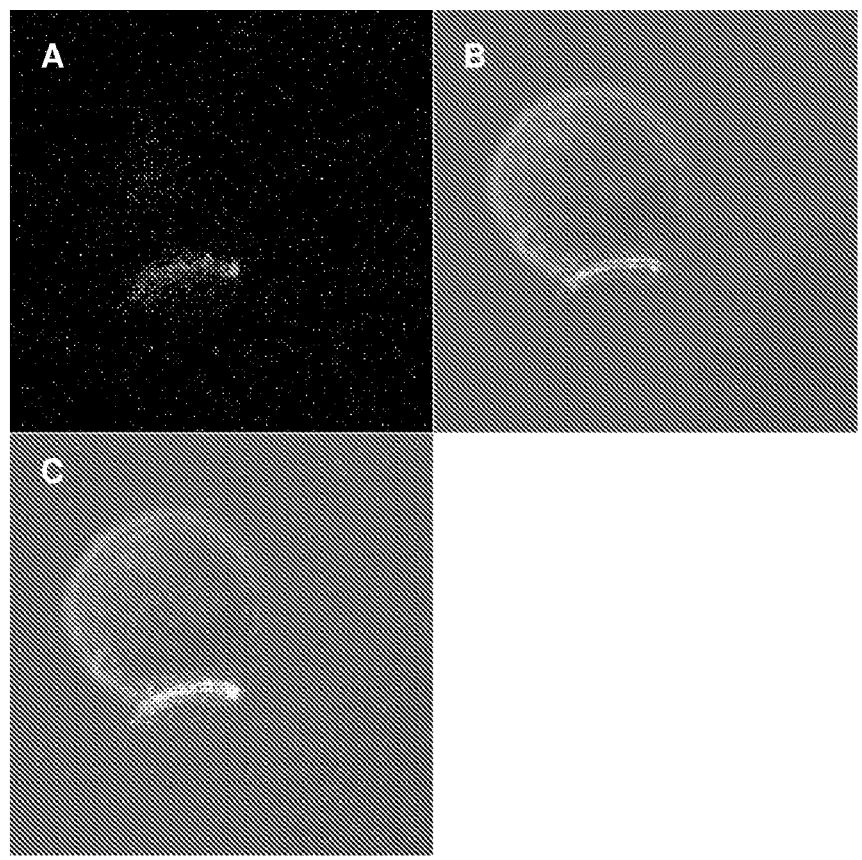
FIGS. 23A-23C are a group of images depicting a fluorescent patch associated with a single cell.

FIG. 20 illustrates the thermal release profile for a PMAA/PNIPAAm release system. On the y-axis is the number of patches remaining on the array after exposure to pH 7.4 PBS for 30 min at the temperature shown on the x-axis. Very clear switching behavior around the LCST of PNIPAAm homopolymer was observed, indicating that the solubility of PNIPAAm primarily determines thermal release behavior of the complexed PMAA/PNIPAAm multilayer.

When using PMAA/PNIPAAm, deposition of the labile layer, and all following layers, must be done at a pH below 6.2 to prevent premature film dissolution and release. Further, if PNIPAAm is used for the release region, the deposition temperature must be below 32° C. to ensure a true polymer solution. For several hydrogen-bonded systems that can be used in the release region a thickness of approximately 250 nm was desirable.

A payload multilayer assembly was deposited on top of the labile layer. This layer of the patch is presented to the extracellular environment after the patch is adhered to a cell and released from the substrate on which it was assembled. Examples of possible cargoes that may be incorporated into this region include drugs, proteins, nanoparticles, environmentally responsive "smart" materials, and imaging contrast agents. See, for example, M. C. Berg, et al., *Biomacromolecules* 7 (1), 357 (2006); Y Lvov, K. Ariga, and T. Kunitake, *Chemistry Letters* (12), 2323 (1994); Y Lvov, et al., *Thin Solid Films* 285, 797 (1996); Z. Z. Wu, et al., *Advanced Materials* 18 (20), 2699 (2006); and Z. Li, et al., *Langmuir* 22 (24), 9820 (2006), each of which is incorporated by reference in its entirety. Anionic, superparamagnetic nanoparticles were alternately deposited with fluorescein-labeled PAH to create a fluorescent labeled and magnetically responsive PEM patch. Ten bilayers of magnetic nanoparticles and fluorescein-labeled PAH yielded a 130 nm thick payload region.

The final region of the assembled heterostructure is the cytophilic layer, anchoring the payload region to the cell membrane. The cytophilic layer must be chosen with consideration of the cells to be functionalized. For example, an (HA/CHI) multilayer can be appropriate for functionalizing lymphocytes, because lymphocytes contain CD44 cell-surface receptors whose natural antigen is a 3-structural unit repeat of the polysaccharide hyaluronic acid (see, e.g., C. Underhill, *J Cell Sci* 103 (2), 293 (1992), which is incorporated by reference in its entirety). Previous work has shown how the molecular configurations of adsorbed weak polyelectrolyte chains, including the relative quantities of loops, trains, and tails, can be controlled using the pH and salt conditions of the polymer solution. See, for example, J. D. Mendelsohn, et al., *Biomacromolecules* 4 (1), 96 (2003); G. J. Fleer, *Polymers at interfaces*, 1st ed. (Chapman & Hall, London; New York, 1993, each of which is incorporated by reference in its entirety. When in solution, a weak polyelectrolyte at a pH equal to the solution pKa will have approximately half of the anionic groups charged. The same polyelectrolyte, when incorporated into an electrostatically crosslinked film, will have an "in-film" pKa that is significantly shifted from the solution pKa. For an HA/CHI film (HA $pK_a$ approximately 2.9) this effect can be used to maximize the number of carboxylic acid-containing D-glucuronic acid sugar units in HA that are uncharged and accessible to bind to CD44 by adjusting the pH of the deposition solution. HA thus forms the outermost layer of the cytophilic layer in each heterostructured surface-bound patch. Chitosan was chosen as a complementary polycation for its biocompatibility when complexed with HA in multilayer films (see, e.g., A. L. Hillberg and M. Tabrizian, *Biomacromolecules* 7 (10), 2742 (2006), which is incorporated by reference in its entirety). Three and a half bilayers of HA and CHI yields a approximately 20 nm thick cell-adhesive region.

An exemplary structure for a fluorescent, superparamagnetic, lymphocyte-adhesive patch can be written as follows: $(PMAA3.0/PNIPAAm3.0)_x(FITC\text{-}PAH3.0/Fe_3O_4\ NP4.0)_y(CHI3.0/HA3.0)_z$, with typical values x=80.5, y=10, and z=3.

Figure 12:
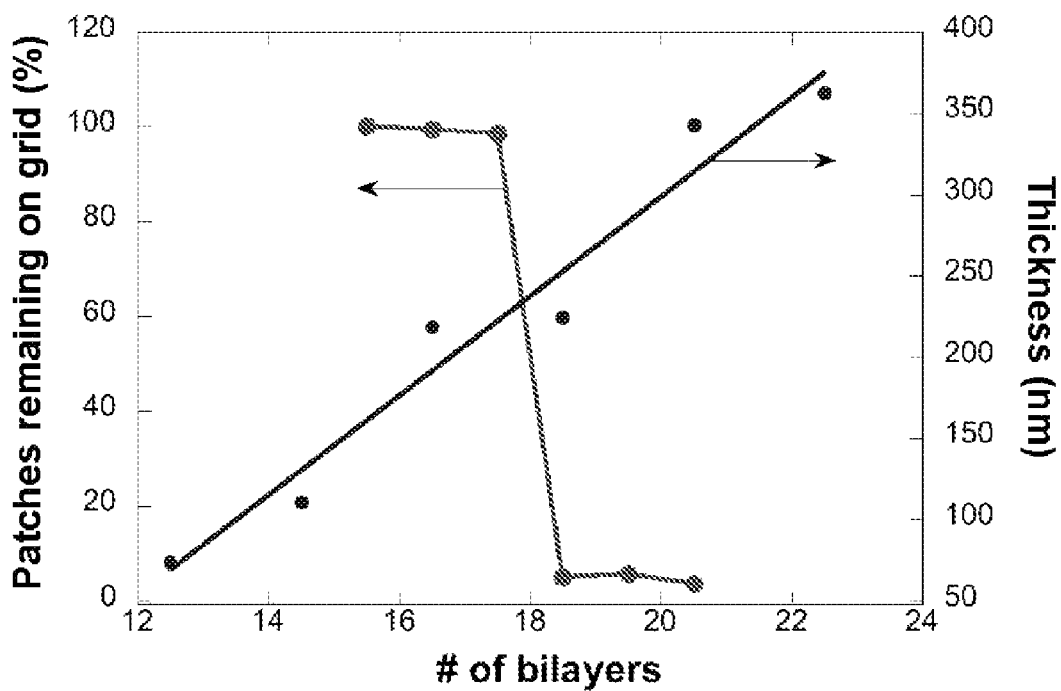
FIG. 12 is a graph depicting patch dissolution behavior.
Figure 13:
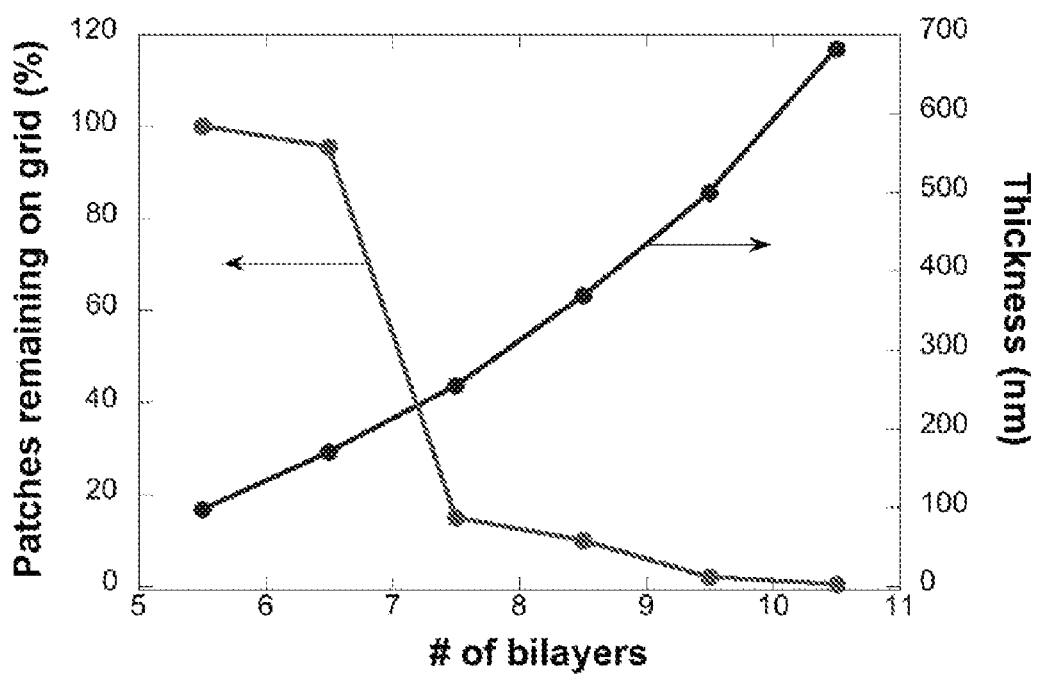
FIG. 13 is a graph depicting patch dissolution behavior.

The conditions that facilitate release of the patch from the surface by the labile layer were investigated. Decher and Ono previously reported that an electrostatic region built on top of a hydrogen-bonded region requires a critical thickness of the hydrogen-bonded region for successful dissolution and release (see, e.g., S. S. Ono and G. Decher, *Nano Lett.* 6 (4), 592 (2006), which is incorporated by reference in its entirety). The release efficiency and release region thickness required for two very different heterostructures, when agitated in PBS for 10 minutes at room temperature, was determined. The two heterostructures considered were as follows: $(PDAC4.0/SPS4.0)_{15.5}(PAA3.0/20\ kMW\text{-}PEG3.0)_{x.5}(PAH3.0/SPS3.0)_{9.5}(HA3.0/FITC\text{-}CHI3.0)_{3.5}$ (see FIG. 12, and $(PMAA3.0/100kMW\text{-}PEG3.0)_{x.5}$ (FITC-PAH3.0/SPS3.0)$_{10}$ (see FIG. 13). The release behavior for each heterostructure showed a precipitous drop at a particular number of bilayers, above which nearly all patches were released. The thickness required for release, approximately 250 nm, was the same in all systems examined, despite differences in polymers and molecular weight, number of bilayers, and electrostatic PEM cap., the. The observed critical thickness suggests that the polycation from the PEM cap was diffusing into the hydrogen-bonded region to compensate the surplus anionic charge found there. This polycation could potentially electrostatically crosslink and stabilize the release region. If the hydrogen-bonded region was thicker than the diffusion path length of the polycation, some non-crosslinked hydrogen-bonded chains remain to dissolve and release the patch Controlling the kinetics of patch release can allow greater flexibility in applications. For instance, some cell types may bind more slowly than others, requiring more time to attach before release; or reproduce very quickly, in which case release must be very fast. A (PAA/PEG) labile layer releases rapidly, on the order of a few seconds, and for many cell types, this is less time than is required for sufficient binding between cell and patch. One method for slowing down the release kinetics of a hydrogen-bonded multilayer film is to increase the salt concentration of the medium. Granick and co-workers have observed that some hydrogen-bonded complexes are stabilized by increasing the ionic strength of the solution (see, e.g., S. A. Sukhishvili and S. Granick, *Macromolecules* 35 (1), 301 (2002), which is incorporated by reference in its entirety). Charge-charge repulsion screening is thought to be the origin of this effect, though this screening must be stronger than the osmotic pressure created by the additional associated ions, which favors film dissolution (see, for example, Eugenia Kharlampieva and Svetlana A. Sukhishvili, *Polymer Reviews* 46 (4), 377 (2006), which is incorporated by reference in its entirety). See the discussion above of the effect of salt concentration displayed in FIG. 14.

Figure 14:
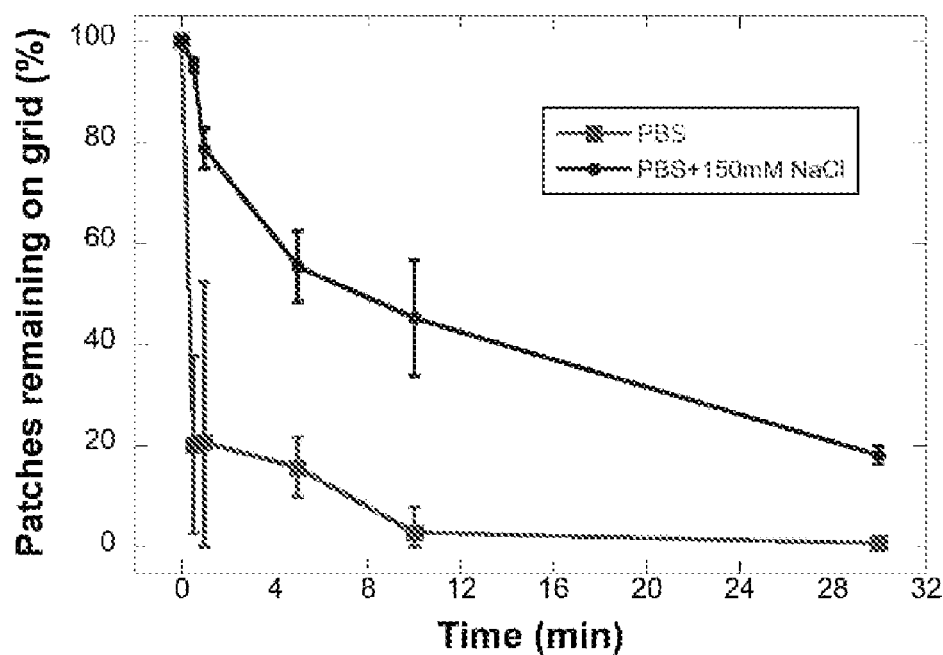
FIG. 14 is a graph depicting patch dissolution behavior.

The time required for patch release was also measured (see FIG. 14). The following heterostructure was considered: $(PDAC4.0/SPS4.0)_{15.5}(PAA3.0/20\text{ kMW-PEG3.0})_{20.5}(FITC-PAH3.0/SPS3.0)_{10}(CHI3.0/HA3.0)_3$. 80% of patches were released within 30 s when agitated in room temperature PBS, and virtually all patches lifted off within 10 minutes. When 150 mM NaCl was added (for a total of approximately 300 mM NaCl), it took 30 min to reach a similar level of release. Error bars reflect the standard deviation among 3 or more patch regions (approximately 300 patches).

Functionalization of B-Lymphocytes

Figure 15:
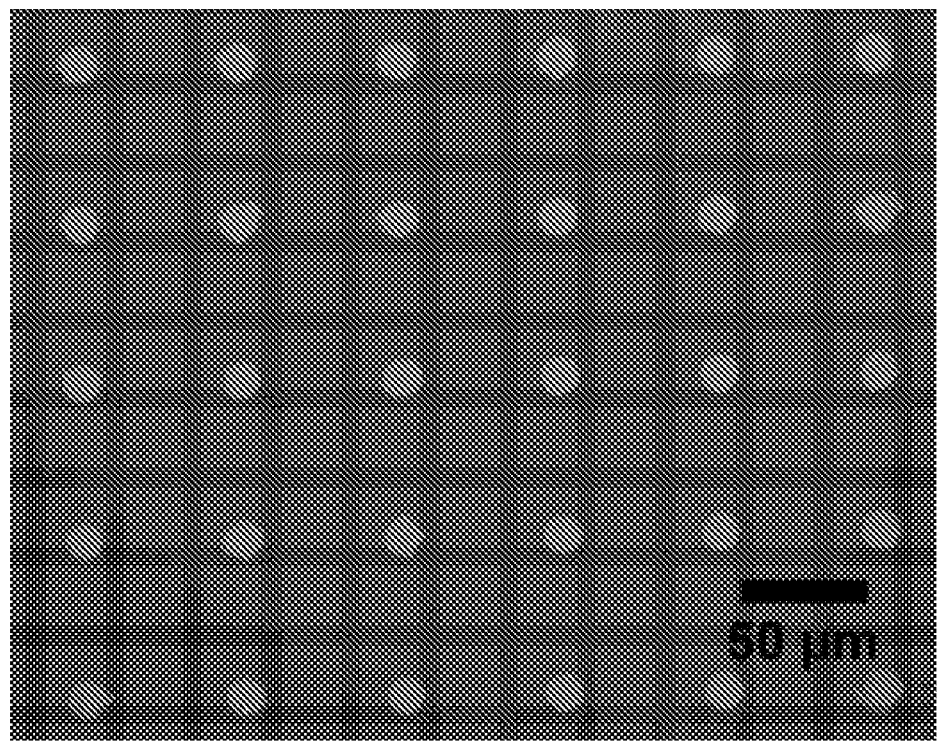
FIG. 15 is a fluorescence micrograph of patches.

Following acetone lift-off, a regular array of surface-bound patches are observed on the glass substrate (see FIG. 15), each of which is now free to anchor to a cell membrane via CD44-HA binding. Preferably, cells settle to the patch-laden surface and associate one cell per patch, though other outcomes are possible. First, there may be more than one cell associated with a patch. Previous studies on colloidal particles adsorbing on patterned surfaces have shown that the ratio between the diameter of the particle and the diameter of a circular feature will determine the cluster size (see, for example, H. Zheng M. F. Rubner P. T. Hammond I. Lee, *Advanced Materials* 14 (8), 572 (2002), which is incorporated by reference in its entirety). During the lithography step, the diameter of the patch can be easily controlled. It was found that with 15 μm diameter patches, many dimers (two cells per patch) resulted, whereas with 10 μm patches, monomers resulted almost exclusively. Next, there are some cells that do not associate with a patch, either because the cell remains in solution or settles onto an 'interstitial' area between patches. Adjusting the density of surface patches and the number of cells in solution can control this number. Additionally, patches may not attach to a cell but will release in the neutral, 4° C. media.

Figure 16:
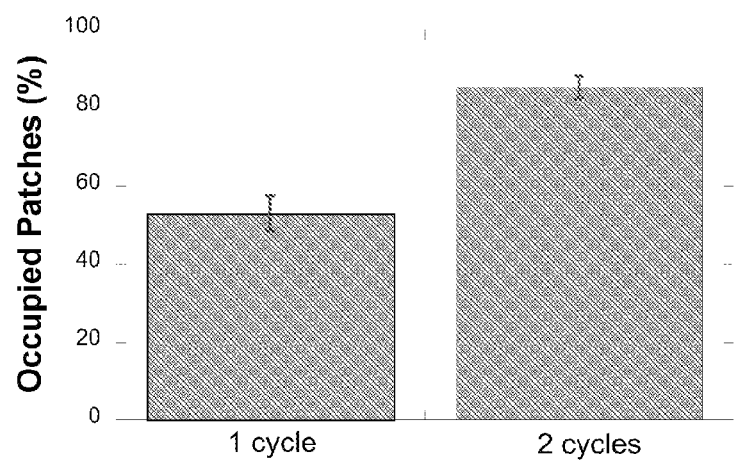
FIG. 16 is a graph depicting patch-cell interaction behavior.
Figure 17A:
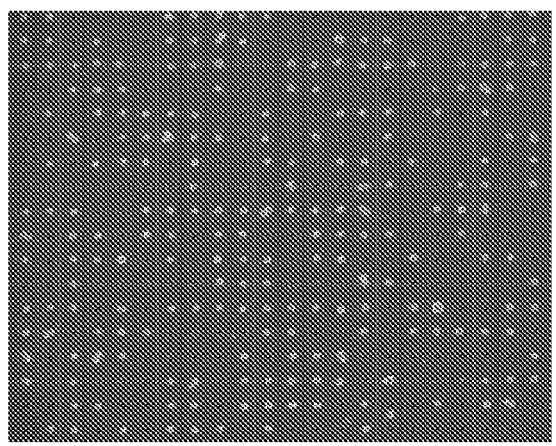
FIGS. 17A-17B are micrographs depicting patch-cell interaction behavior.
Figure 17B:
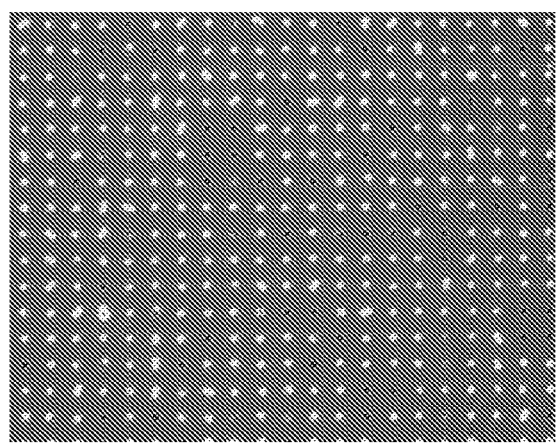

The relative frequency of these scenarios was investigated by fabricating patches without a labile layer, and surveying the cell attachment behavior to the patches and surface interstitial areas. FIG. 16 shows that for the patch system $(Fe_3O_4 \text{ NP4.0/FITC-PAH3.0})_{10.5}(CHI3.0/HA3.0)_3$, 53±5% of patches were occupied after 1 agitation/incubation cycle, and that 85±3% were occupied after 2 cycles (see FIGS. 17A-17B for representative optical micrographs of these two scenarios). Previous attempts to immobilize and pattern non-adherent CH27 B-cells required numerous steps involving polymer stamping, antibodies, and non-selective attachment of biotin to the cell surface (see, for example, H. Kim, et al., *Advanced Functional Materials* 16 (10), 1313 (2006); and H. Kim, et al., *Biomacromolecules* 5 (3), 822 (2004) each of which is incorporated by reference in its entirety). Here, a straightforward method for non-adherent cell patterning based solely upon the natural interaction between CD44 and HA is provided, with an efficacy that rivals the previous method.

An important design parameter is the balance between cell adhesion and dissolution of the labile layer. The strength of the interaction between the cell and the cell-adhesive layer is desirably greater than that between the functional and release regions. If the patch lifts off the substrate before a cell is able to bind, the likelihood of the patch encountering a cell (while both are floating freely in dilute solution) is very low. Other options for cell-patch interaction exist, such as non-selective biotin/streptavidin or RGD-integrin strategies. See, for example, H. Kim, et al., *Advanced Functional Materials* 16 (10), 1313 (2006); H. Kim, et al., *Biomacromolecules* 5 (3), 822 (2004); and M. C. Berg, et al., *Langmuir* 20 (4), 1362 (2004), each of which is incorporated by reference in its entirety. Temperature also plays a role in mediating the cell-patch and labile layer dissolution. Lymphocytes did not attach to HA-containing surfaces at 4° C., and most efficiently bound at 37° C. Using an LCST-based labile layer allows us to attach the cells at a temperature optimal for encouraging attachment and preventing release. The temperature can then be very briefly lowered below the LCST to encourage patch release, and then the cells returned to physiological temperature.

Figure 18:
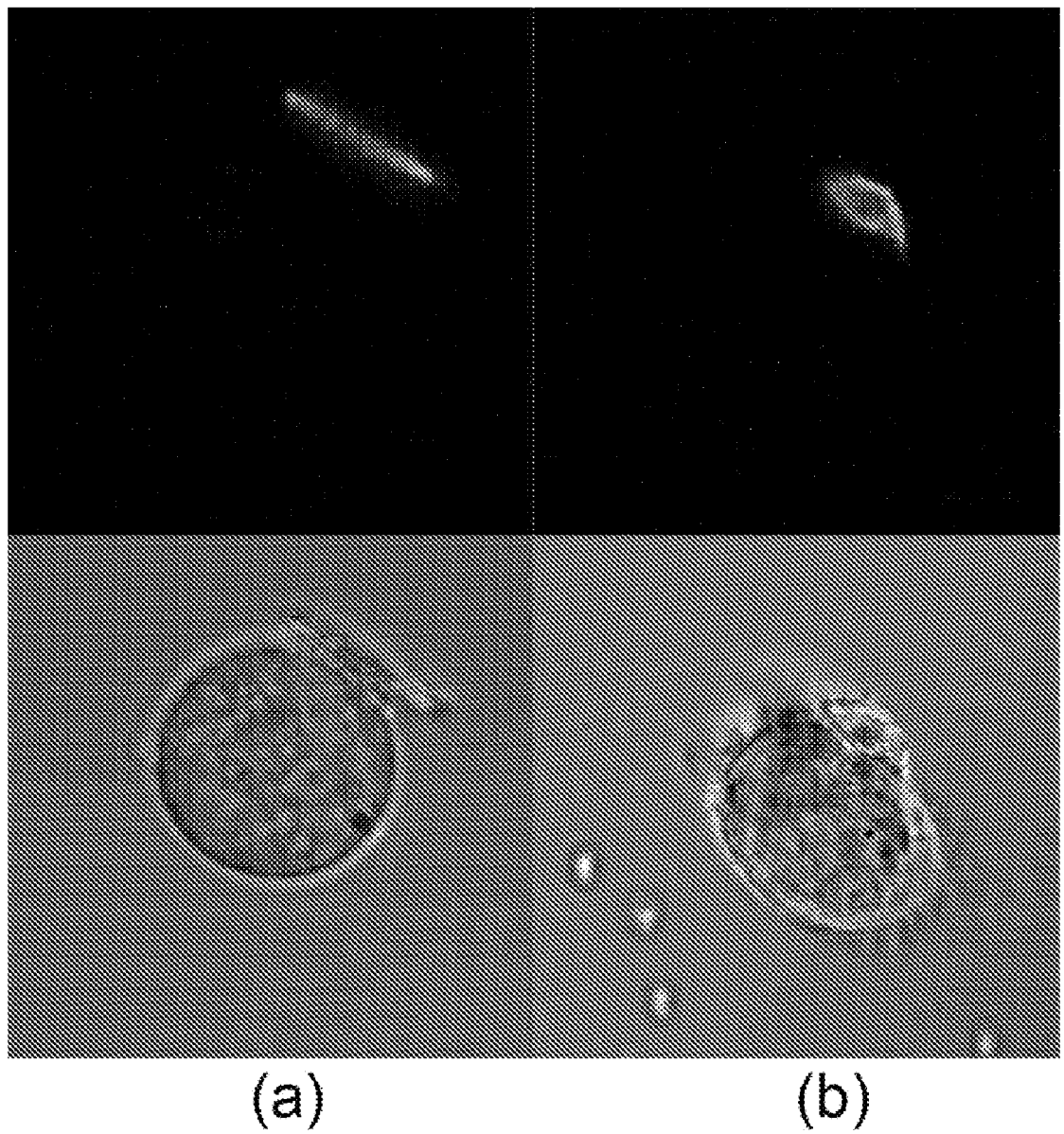
FIG. 18 is a group of images depicting a fluorescent patch associated with a single cell.

FIG. 18 shows CLSM optical brightfield and fluorescence images of a patch on the surface of two live lymphocytes suspended in media immediately after patch attachment. FIG. 18a shows a patch attached to the surface of a CH27 B-lymphocyte, and FIG. 18b is a HuT78 T-lymphocyte.

Figure 19:
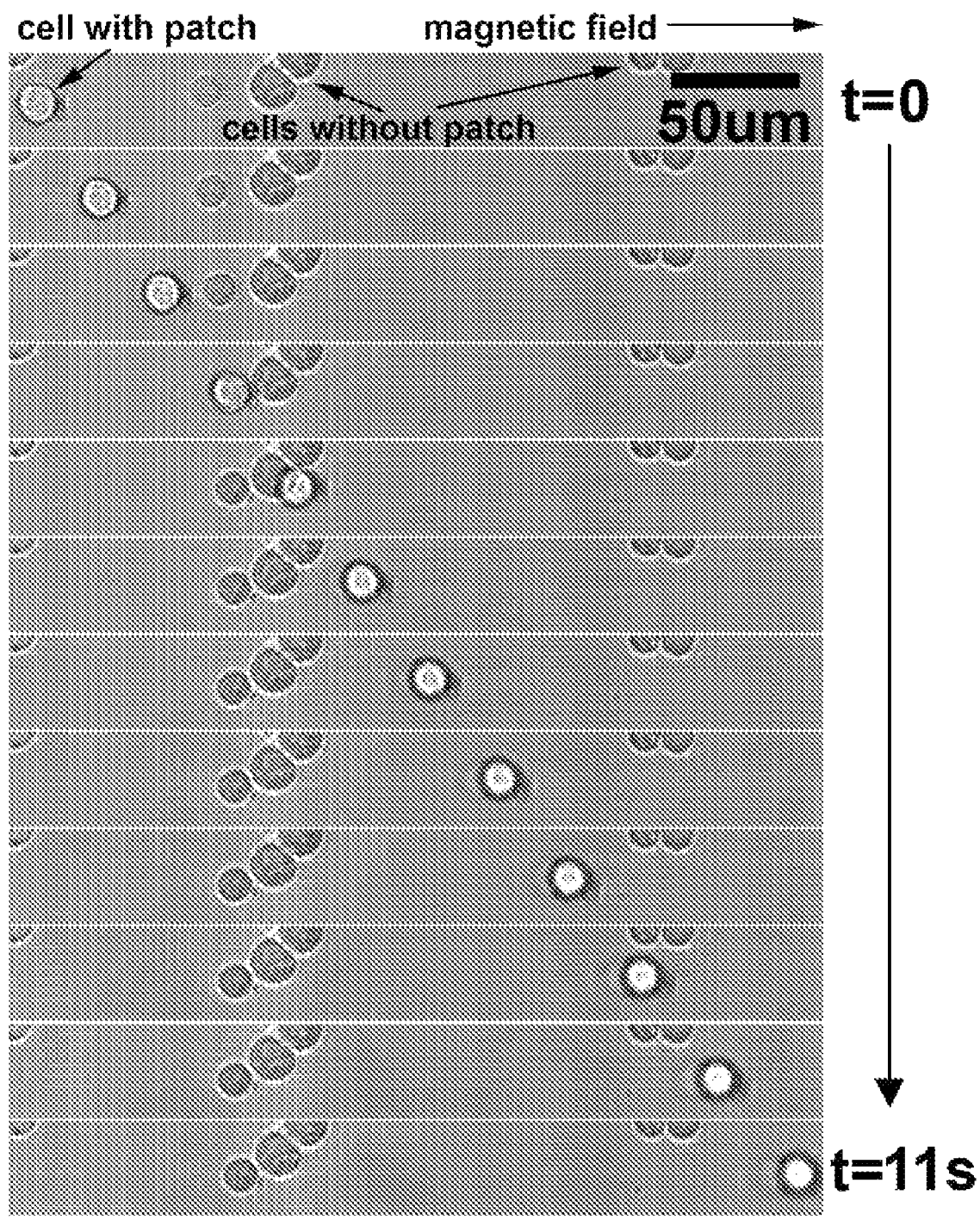
FIG. 19 is a time sequence of images depicting a magnetic patch associated with an individual cell.

To test that magnetic properties were conferred on the cell via the attached patch, B-lymphocytes were exposed to superparamagnetic patches containing a PMAA/PVPON-release region. The free-floating lympocytes were imaged in a LabTek chamber using an inverted microscope. After cells were allowed to settle, a rare earth magnet was placed close to the imaged region but outside of the chamber. FIG. 19 shows how a CH27 cells responds to the applied magnetic field as a result of the membrane-bound patch. This cell moved a total of approximately 200 μm in 11 seconds, but moves out of the focal plane during the course of imaging.

Using commercially available amino-functionalized quantum dots (600 nm emission), the patches were prepared according to the following: $(PMAA3/PNIPAAm3)_{x.5}(\text{QuantumDots5/SPS5})_{30}(PAH4/MNP4)_{10}(CHI3/HA3)_3$ where x is 20, 40, 60 or 80 (MNP=magnetic nanoparticles). Neutral pH conditions resulted in successful release. FIGS. 21A-21C, 22A-22C, and 23A-23C are micrographs of the patches in the absence (FIG. 21) or presence (FIGS. 22 and 23C) of CH27 B-cells. In these figures, panel A is a fluorescence image, panel B is a bright field micrograph of the same subject, and panel C is a merged image of panels A and B.

The hyaluronic acid-CD44 interaction was effective for associating patches with cells (e.g., B cells) displaying CD44 on the cell surface. However, not all cell types display CD44, and so a more general mechanism of association can be desirable. Nearly all cell types bear free thiol (—SH) groups on the cell surface. Thiol groups can react with other functional groups (such as, e.g., a maleimide group) and this reactivity can be used to form a covalent bond between a patch and the cell surface.

In particular, a patch may be exposed to a crosslinking reagent prior to be exposed to cells. The crosslinking reagent can be chosen to have two reactive groups with differing reactivity, so that one reactive group can form a covalent bond with a functional group found in the patch, and the other reactive group can form a covalent bond with a thiol group. For example, the crosslinking reagent can include an amine-reactive functional group (such as, for example, an N-hydroxysuccinimide group, capable of reacting with amine groups in, for example, PAH) and a thiol reactive group. Other suitable reactive groups and crosslinking reagents are known.

Figure 24:
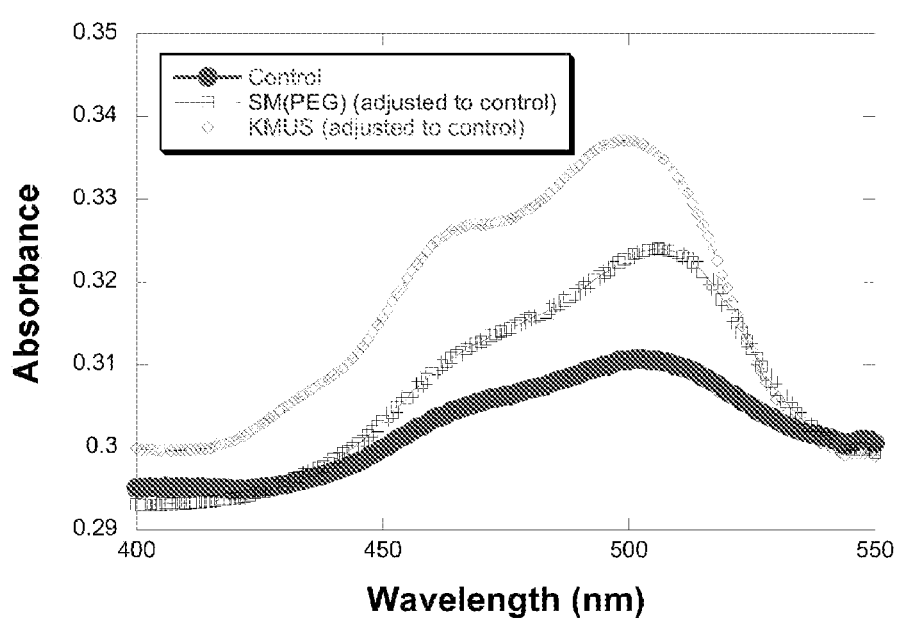
FIG. 24 is a graph depicting optical properties of patches.

Patches were exposed to heterobifunctional crosslinking reagents, and subsequently to a free-thiol containing fluorescent dye. The absorbance of this dye was measured for different heterobifunctional crosslinkers, and it was found found that the maleimide group was covalently attached to the patch. FIG. 24 plots absorbance intensity of patches after crosslinking to the dye, showing that both heterobifunctional crosslinkers successfully presented thiol-reactive maleimide groups. The crosslinking regeants used were N-[κ-maleimidoundecanoyloxy]sulfosuccinimide ester (sulfo-KMUS) and succinimidyl-[(N-maleimidopropionamido)-octaethyleneglycol]ester (SM(PEG)$_8$), both available from Pierce Biotechnology. Other crosslinking reagents are commercially available, from Pierce and other suppliers.

Figure 25:
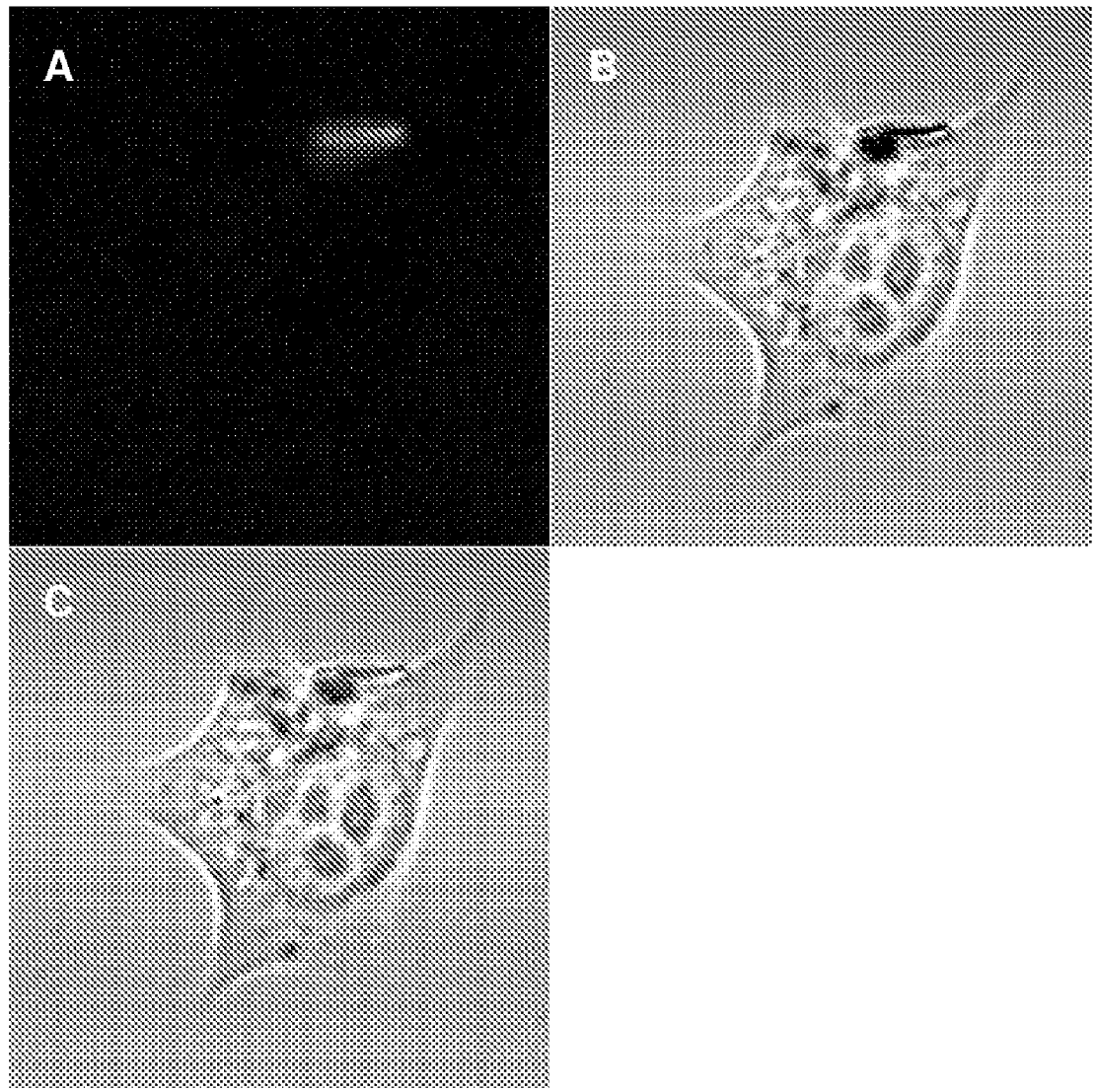
FIGS. 25A-25C are a group of images depicting a fluorescent patch associated with a single cell.
Figure 26:
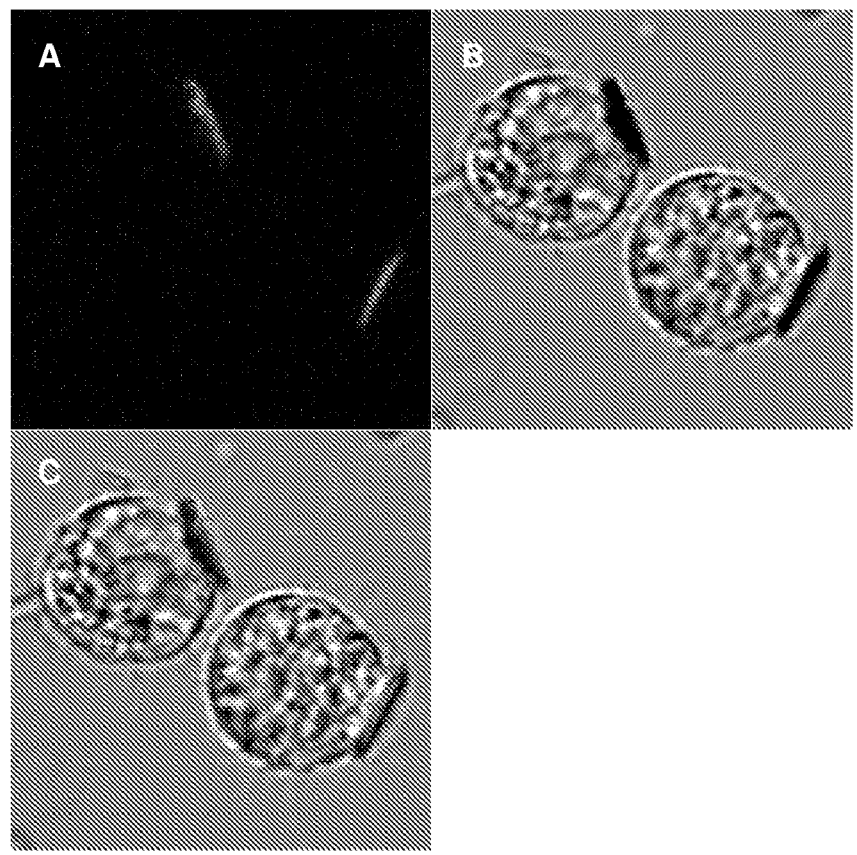
FIGS. 26A-26C are a group of images depicting a fluorescent patch associated with a single cell.

A covalent linking approach was used to associate patches with dendritic cells, another type of immune cell. Dendritic cells belong to a large class of cells called antigen-presenting cells, or APCs, which are known to be phagocytotic. In general, these cells will internalize and digest anything found in their environment, presenting fragments of resulting antigens on their surface, in turn stimulating further immune system responses. FIGS. 25A-25C are micrographs of a (PMAA3/PNIPAAm3)$_{80.5}$ (PAH4/MNP4)$_{10}$(CHI3/HA3)$_3$ patch associated with a dendritic cell spread on a tissue culture polystyrene (TCPS) dish (panel A, a fluorescence image; panel B bright field microscopic image of the same subject; and panel C, merged image of panels A and B). FIGS. 26A-26C are micrographs of a (PMAA3/PNIPAAm3)$_{80.5}$ (PAH4/MNP4)$_{10}$ patch associated with a dendritic cell on a PDAC-terminated background.

Unlike nano- or microparticle based delivery systems, these phagocytes did not internalize the patches. Cells were observed with patches attached, then being released from the cell surface, and then being picked up again. Cells with patches attached were also observed to phagocytose small polystyrene beads, demonstrating that the cell was still able to perform its native function (phagocytosis) without interference from the patch. It also demonstrated that the patch can remain exposed to the extracellular environment and able to deliver drug, adjuvants, or antigens to the local surroundings while the cell remains able to phagocytose and process antigens for presentation.

Figure 27:
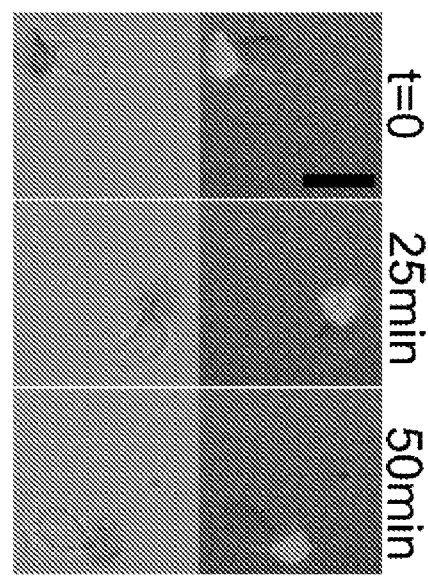
FIG. 27 is a time sequence of images depicting a magnetic patch associated with an individual cell.

Association of a patch with an immortalized human T-cell did not impair the cell's native migration capabilities. After association, the cell was allowed to migrate on a protein-coated coverslip and observed microscopically. The cell was still able to migrate, and always kept the patch on the trailing end of the cell. This cell was seen to migrate for several hours with the pactch attached. Images of this T cell recorded at three different time points are found in FIG. 27.

Other embodiments are within the scope of the following claims.

What is claimed is:

1. A polymer structure arranged on a substrate, comprising:
a substrate-adhering layer;
a labile layer configured to selectively dissociate under predetermined conditions arranged over the substrate-adhering layer; and
a cytophilic layer arranged over the labile layer, the cytophilic layer having a specific affinity for a surface of a predetermined cell type;
wherein the cytophilic layer has a surface area smaller than a cell of the predetermined cell type.

2. The structure of claim 1, further comprising a diffusion barrier layer arranged intermediate to the labile layer and the cytophilic layer.

3. The structure of claim 1, further comprising a functional layer arranged intermediate to the labile layer and the cytophilic layer.

4. The structure of claim 1, wherein the substrate-adhering layer includes a polyelectrolyte multilayer.

5. The structure of claim 1, wherein the labile layer includes a hydrogen-bonded polymer multilayer.

6. The structure of claim 5, wherein the cytophilic layer includes a polyelectrolyte multilayer.

7. A polymer structure arranged on a substrate, comprising:
a substrate-adhering layer including a polyelectrolyte multilayer;
a labile layer including a hydrogen-bonded polymer multilayer arranged over the substrate-adhering layer; and
a cytophilic layer including a polyelectrolyte multilayer arranged over the labile layer, the cytophilic layer having a specific affinity for a surface of a predetermined cell type;
wherein the cytophilic layer has a surface area smaller than a cell of the predetermined cell type.

8. The structure of claim 7, further comprising a diffusion barrier layer including a polyelectrolyte multilayer arranged intermediate to the labile layer and the cytophilic layer.

9. The structure of claim 7, further comprising a functional layer including a polyelectrolyte multilayer arranged intermediate to the labile layer and the cytophilic layer.

10. The structure of claim 7, wherein the cytophilic layer includes a ligand for a cell surface receptor of the predetermined cell type.

11. The structure of claim 7, wherein the labile layer is configured to dissolve under conditions conducive to binding of the cell to the cytophilic layer.

12. The structure of claim 7, wherein the structure is a member of a population of substantially identical polymer structures arranged on the substrate.

13. The structure of claim 7, wherein the structure has lateral dimensions in the range of 1 μm to 250 μm and a thickness in the range of 50 nm to 1 μm.

14. The structure of claim 7, wherein the structure has lateral dimensions in the range of 1 μm to 100 μm.

15. The structure of claim 7, wherein the structure has lateral dimensions in the range of 1 μm to 50 μm.

16. A method of making a composition, comprising:
forming a polymer structure arranged on a substrate, the polymer structure including:
a substrate-adhering layer including a polyelectrolyte multilayer;
a labile layer including a hydrogen-bonded polymer multilayer arranged over the substrate-adhering layer; and
a cytophilic layer including a polyelectrolyte multilayer arranged over the labile layer, the cytophilic layer having a specific affinity for a surface of a predetermined cell type;
wherein the cytophilic layer has a surface area smaller than a cell of the predetermined cell type; and
contacting the polymer structure with a cell of the predetermined cell type, thereby forming a cell-patch-substrate association; and
causing the labile layer to release a cell-patch association from the substrate.

17. The method of claim 16, wherein contacting the polymer structure with a cell of the predetermined cell type occurs under conditions in which the labile layer is substantially soluble.

18. The method of claim 16, wherein the polymer structure further includes a diffusion barrier layer including a polyelectrolyte multilayer arranged intermediate to the labile layer and the cytophilic layer.

19. The method of claim 16, wherein the polymer structure further includes a functional layer including a polyelectrolyte multilayer arranged intermediate to the labile layer and the cytophilic layer.

20. The method of claim 16, wherein the cytophilic layer includes a ligand for a cell surface receptor of the predetermined cell type.

21. The method of claim 16, wherein the structure is a member of a population of substantially identical polymer structures arranged on the substrate.

22. The method of claim 16, wherein causing the labile layer to release a cell-patch association from the substrate includes dissociating the labile layer.

23. The method of claim 16, wherein causing the labile layer to release a cell-patch association from the substrate includes exposing the patch to a solution with a predetermined pH capable of dissociating the labile layer.

24. The method of claim 16, wherein causing the labile layer to release a cell-patch association from the substrate includes exposing the patch to a solution with a predetermined temperature capable of dissociating the labile layer.

25. The method of claim 16, wherein contacting the polymer structure with a cell of the predetermined cell type occurs before causing the labile layer to release a cell-patch association from the substrate.

26. The method of claim 16, wherein contacting the polymer structure with a cell of the predetermined cell type occurs simultaneously with causing the labile layer to release a cell-patch association from the substrate.

27. The method of claim 16, wherein contacting the polymer structure with a cell of the predetermined cell type occurs after causing the labile layer to release a cell-patch association from the substrate.

\* \* \* \* \*